US011857692B1

(12) United States Patent
Siegert Scherer

(10) Patent No.: US 11,857,692 B1
(45) Date of Patent: Jan. 2, 2024

(54) TUNABLE OUTPUT IRRADIANCE SYSTEM

(71) Applicant: Roberto Siegert Scherer, Austin, TX (US)

(72) Inventor: Roberto Siegert Scherer, Austin, TX (US)

(*) Notice: Subject to any disclaimer, the term of this patent is extended or adjusted under 35 U.S.C. 154(b) by 0 days.

(21) Appl. No.: 18/153,736

(22) Filed: Jan. 12, 2023

Related U.S. Application Data

(60) Provisional application No. 63/411,796, filed on Sep. 30, 2022.

(51) Int. Cl.

| | |
|---|---|
| ***A61L 2/00*** | (2006.01) |
| ***A62B 7/08*** | (2006.01) |
| ***G01N 21/00*** | (2006.01) |
| ***G01N 23/00*** | (2006.01) |
| ***A61L 2/24*** | (2006.01) |
| ***H05B 47/105*** | (2020.01) |
| ***A61L 9/20*** | (2006.01) |
| ***A01G 7/04*** | (2006.01) |
| ***G05B 13/02*** | (2006.01) |

(52) U.S. Cl.
CPC ................ *A61L 2/24* (2013.01); *A01G 7/045* (2013.01); *A61L 2/0047* (2013.01); *A61L 9/205* (2013.01); *G05B 13/027* (2013.01); *H05B 47/105* (2020.01); *A61L 2209/111* (2013.01); *A61L 2209/12* (2013.01)

(58) Field of Classification Search
CPC ..... A61L 2/08; A61L 2/10; A61L 9/00; A61L 9/18; A61L 9/20; A61L 9/205; A61L 2202/25; A61L 2209/11; A61L 2209/16
USPC ..... 422/23–24, 120, 124, 186.3; 250/454.11, 250/455.11
See application file for complete search history.

(56) References Cited

U.S. PATENT DOCUMENTS 5,933,702 A * 8/1999 Goswami .................. F24F 3/12 422/186.3
8,895,939 B2 * 11/2014 Lyslo ........................ A61L 2/24 422/23

* cited by examiner

*Primary Examiner* — Monzer R Chorbaji
(74) *Attorney, Agent, or Firm* — Lee & Hayes, P.C.

(57) ABSTRACT

A system including groups of illuminators configured to provide adaptive irradiance within the ultraviolet spectrum to remove pathogens, particles, and anthropogenic activity from an air mass of a physical environment based on a detection of a presence of and amount of pathogens, particles, and anthropogenic activity in the air mass.

20 Claims, 20 Drawing Sheets

900
802
804
804
804
808
806

TUNABLE OUTPUT IRRADIANCE SYSTEM

CROSS-REFERENCE TO RELATED APPLICATION(S)

This application claims priority to U.S. Provisional Application No. 63/411,796, filed on Sep. 30, 2022 and entitled "Tunable Output Irradiance Wide-Spectrum Adaptive and Autonomous UV Luminaire or System Incorporating Decoupled and Independent UV Light Sources with Distinctive Spectral Responses," the entirety of which is incorporated herein by reference.

BACKGROUND

Use of systems for clearing and removing pathogens and bacteria from the environment has increased in various different sectors throughout the United States in recent years. However, conventional systems are typically directed to specific wavelengths, specific use or industries, and remain on during the systems lifespan. However, even in specific use scenarios, air and/or water quality or conditions that may vary and, accordingly, the systems may require different dosage regimens, power settings, or the like.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

Figure 1:
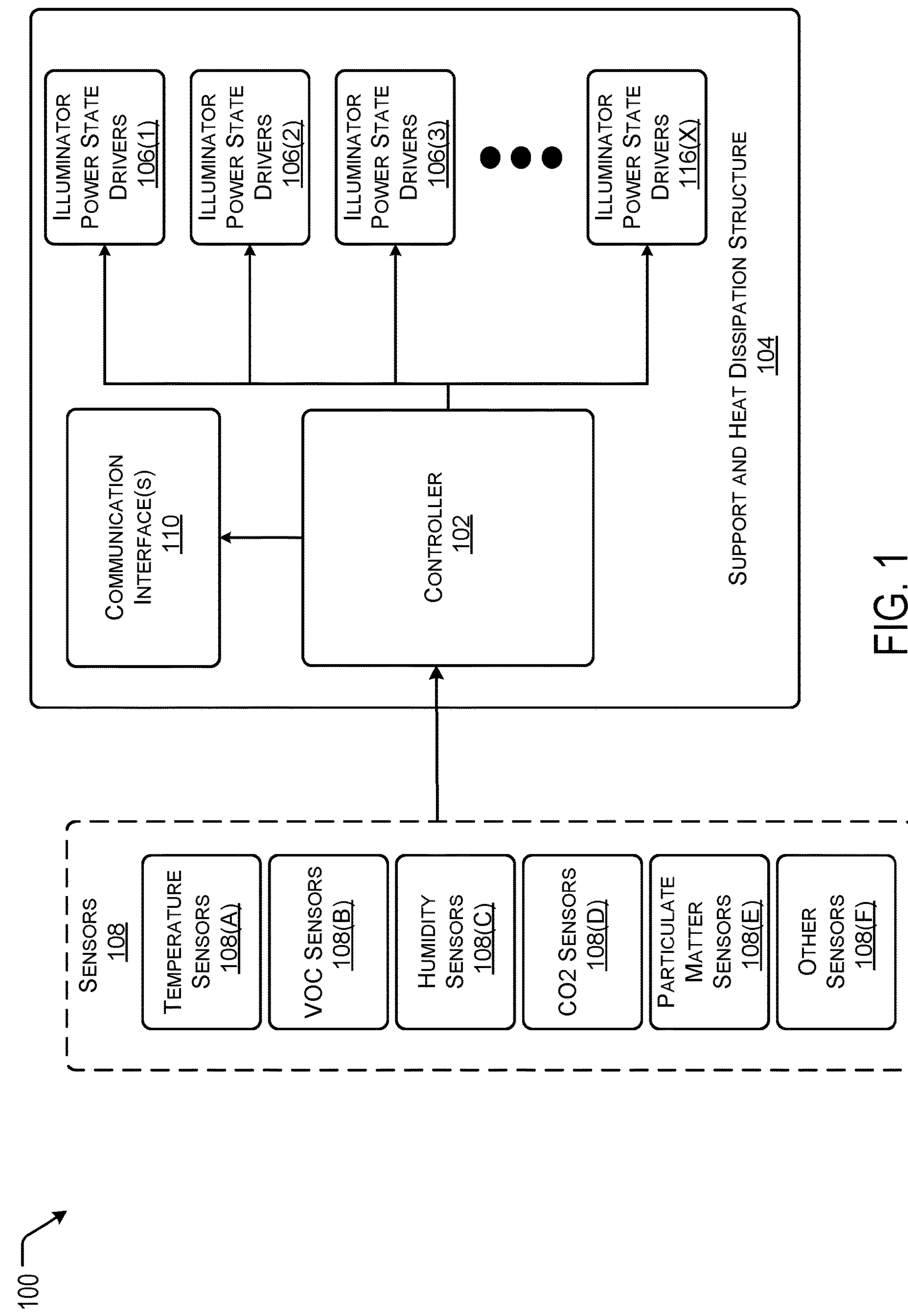
FIG. 1 is an example pictorial diagram of an environmental quality system according to some implementations.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Discussed herein are systems and methods associated with automating, optimizing, and customizing air and/or water quality and cleaning solutions. For example, in some cases, an autonomous system may be configured to provide tunable output irradiance via ultraviolet (UV) luminaries. In other cases, the autonomous system may be configured to provide independent and decoupled UV light sources or luminaries with distinctive spectral responses. In this manner, the systems, discussed herein, allow for combining different light sources in the same structure, expanding functionality of a single system, reducing power consumption, and increasing overall lifespan of environmental quality systems.

In an example implementation, the environmental quality system may include one or more luminaires coupled to a controller for providing tunable irradiance. In some cases, the controller may be configured to allow an operator to tune the irradiance or light output by the luminaries within specific spectrum ranges based on, for instance, an intended use of the environmental quality system, characteristics of an environment of the system, an industrial or business purposes of an associated facility, or the like. In some cases, the controller may be in communication with a user device and/or cloud based service to allow the operator to tune or otherwise update, edit, or change settings or characteristics associated with the irradiance output by the luminaries.

In some examples, the environmental quality system may also be equipped with one or more sensors to detect or capture data associated with one or more environmental conditions associated with the system. For example, the system may be equipped with temperature sensors, humidity sensors, volatile organic compound (VOC) sensors, carbon dioxide sensors, particulate matter sensors, or the like. The data generated by the sensors may be provided to the controller and/or the cloud based service to detect the presence and/or determine identity of any anthropogenic activity, contaminants, components or compounds derived from the anthropogenic activity, and/or other compounds of interest present in the surrounding environment. The controller and/or cloud based service may then automatically tune or update the characteristics of the irradiation output by the system based on the current level anthropogenic activity, contaminants, and/or compounds of interest. For example, the controller or cloud based service may tune the characteristics of the irradiation output based on one or more predetermined heuristic and/or based on the output of one or more machine learned models or networks trained using the captured sensor data, data associated with anthropogenic activity, characteristics of the irradiation output, and/or the like.

In some examples, the system may be configured to activate and deactivate the illuminators in response to the presence, levels, amount, percentage, density, concentrations of anthropogenic activity and/or contaminants, or the like in the surrounding environment. For example, if the concentration of anthropogenic activity meets or exceeds one or more thresholds, the system may activate or enable the illuminators to commence cleaning functions. Likewise, if the anthropogenic activity falls below the one or more thresholds or one or more additional thresholds, the system may deactivate or disable the illuminators (it should be understood that the activation and deactivation thresholds may differ). In this manner, the system may provide need based cleaning that may prolong the usable lifespan of the illuminators and, accordingly, the system, thereby reducing overall installation costs. Additionally, by disabling the illuminators when the anthropogenic activity is low (e.g., below the designated thresholds), the system may also reduce the overall operating expenses associated with the environmental quality system.

In some examples, the illuminators may be polychromatic light sources that operate within a wide UV spectrum. The system may also, in addition to or lieu of the polychromatic light sources, include illuminators within the visible spectrum that may be used in combination and tuned to distinctive bands of the UV spectrum. In one specific example, the system may utilize a group of ultraviolet A (UVA) illuminators, a group of ultraviolet C (UVC) illuminators, a group of far UV excimer illuminators, and a group of low pressure mercury vapor illuminators. In this manner, the system may utilize illuminators that are less expensive to install, have lower operating costs (e.g., energy consumption), and increased life span when compared with conventional systems.

In some cases, the system may also include one or more surfaces exposed to the illuminators that are coated or otherwise treated with a photocatalytic oxidizing (PCO) coating to assist with the PCO processes that apply to air and/or water applications by modulating distinctive irradiation spanning from the UVA bands through, for example, the UVC bands. For example, the surfaces may be coated with a catalyst, such as titanium dioxide which causes a reaction with UVC (and/or UVA) irradiation that converts the components derived from the anthropogenic activity, targeted contaminants or undesired chemical compounds into water, carbon dioxide, and/or other harmless detritus. In some cases, the coated surfaces may be a replaceable or removable section of the system, such as discussed in more detail below, that may allow for replacement or recoating to maintain desired levels of catalyzation with the UVC (and/or UVA) irradiation.

In some cases, the environmental quality system may also be equipped with germicidal components that may operate concurrently with but in a decoupled fashion from the PCO components. For example, in some specific implementation, the environmental quality system may include a forced ventilation stage that utilizes a metallic impeller or other high temperature resistant material that may be irradiated by the illuminators to cause a reaction that may disinfect the air. In some cases, the impeller may be heat treated (calcination at about 500 degrees Celsius) after a nanostructured ceramic coating (e.g., titanium dioxide) is applied onto the surface using a known industrial coating processes. As an alternative, a polymeric impeller may be utilized and coated with a ceramic coating via a sol-gel method and treated at lower temperatures than a metallic impeller.

In one example, the impeller or similar component is irradiated or illuminated by the UV light source tuned to one or more UV bands in order to activate the photocatalytic oxidation or PCO response of the nanostructured ceramic layer. Under these operating conditions, the environmental quality system generates hydroxyl radicals that constitutes a mechanism responsible for the air and/or water purification functionality of the current example. In some cases, UVC or germicidal light sources or illuminators may be placed within a chamber housing with the fan impeller as well as in an intake and exhaust manifold/ducts associated with the environmental quality system in order to disinfect the air or water flowing through the system at multiple locations. In some implementations, the system may be configured to project UVC light outwards (such as upwards) and along the laminar flow patterns defined by the exhaust geometry. In this manner, the system may act as a chamber-based air or water disinfection unit as well as an upper-air disinfection unit. Furthermore, the UVC light source can be installed onto a motorized actuator allowing it to be oriented inwards, towards the chamber inner walls, or outwards, based on the operating conditions described above.

In some implementations, a controller balances the dosage of UV irradiance applied to the impeller or other PCO elements. In some cases, the system may be equipped with sensors to generate data that may be utilized to correlate and/or determine anthropogenic activity (such as CO2 sensors and particle matter PM 1.0, 2.5 and 10.0 micrometers). The determined anthropogenic activity may then be used by the controller to govern the germicidal irradiance/dosage regime (such as via an output of a machine learned model or network, hierarchal design, thresholding, or the like).

The above-described operation of the embodiment addresses the important mismatch in life-span and reliability performance between UVC and UVA light sources of conventional systems. The environmental quality system, discussed herein, may maintain strict control over the individual UV band irradiance/dosage to drastically increase the reliability performance of the system and extend its overall life-span in comparison to conventional systems.

In some implementations, in addition to servicing as an environmental quality system, the systems discussed herein may operate as a horticultural system. For instance, in these examples, the controller exerts direct control over visible-spectrum, UVA, UVB, UVC and/or far-UV illuminators, as discussed herein, in order to exploit growth cycles of the crops (photo morphology and photoperiodicity). In these cases, the use of specialized sensors or detectors (e.g., a multi-range particulate matter sensor) allows for the controller to adjust a germicidal dosage when airborne particulates are detected (which positively correlate to the presence of spores responsible of powdery mildew deposits). In this manner, the horticultural system may apply ad-hoc germicidal treatment of an air or water mass nearby the crops only when the airborne spores and/or pollen grains are detected. Under other operating condition, the horticultural system may be used for surface disinfection of the plant tissues and nearby surfaces in order to contain the spread of some powdery molds, spider mites, other microorganisms, and/or the like.

In the horticultural system, the horticultural illuminators will have a form factor similar to the environmental quality systems discussed below with respect to FIGS. 1-20. In these cases, the illuminators or light sources may be oriented towards the actual crops, the PCO engine may make use of an elongated cross-flow impeller moving air upwards and through the actual system, while allowing for the mass of air exhausted via the system to be exposed to the irradiance of germicidal illuminators. In some cases, a portion of the housing of the horticultural illuminators may also house UV illuminators (e.g. UVB illuminators combined with UVC illuminators) that may influence the growth cycle of the crop and may be used to irradicate mites and other pathogens.

FIG. 1 is an example pictorial diagram of an environmental quality system 100 according to some implementations. In the current example, the environmental quality system 100 may include a controller 102 mounted on a support and heat dissipation structure 104 together with illuminators and/or illuminator power state drivers 106(1)-(X). In some examples, the support and heat dissipation structure 104 may include a mechanical support structure that defines a shape and overall form factor of the assembly of the system 100. The structure 104 may also serve for heat extraction and, accordingly, be constructed out of metal or a heat conductive polymer. The support structures 104 may define the array of illuminators as far as positioning and orientation of individual light sources.

The support structure 104 also provides couplings or components for the installation of the system 100, such as using hooks, bars, brackets and other known attachment components. In some examples, the support structure 104 may be installed as an auto-supported configuration or stand-alone system. The support structure 104 may also constitute a sub-system assembly that is designed as a drop-in solution that accommodates standard form factors such as troffers, high-bay and low-bay configurations, as well as bulb-like shapes.

The support structure 104 also defines the points of attachment for external covers, weather-proofing components, lenses such as focusing lenses, reflectors and/or diffusers. The support structure 104 may also, in some examples, serves as a structure for the adaptation of exoskeletons and/or similar mechanical structures. An example of an adaptation may include the use of a stationary or articulated mounting bracket that support one or a plurality of forced ventilation devices, such as one or more fans or blades.

In the current example, the drivers 106 may be configured to provide power or otherwise energize the illuminators at a level based on one or more signals generated by the controller 102. For example, the drivers 106 may be onboard the illuminators and/or external power sources proximate to the illuminators, such as direct current (DC) power supplies, specialized drivers (e.g., constant-voltage, constant-current, a combination thereof, or other configurations as used in the solid-state lighting industry). In some cases, the drivers 106 may have higher voltage output capabilities, such as to excite gas discharge devices, such as low- and medium-pressure lamps, as well as the electrostatic discharge devices. In some cases, the drivers 106 may include ferro-resonance topologies, fly-back converters in various configurations (such as discontinued-mode, critical-conduction mode and continuous-mode, single-ended primary-inductance converters (SEPIC), boost and buck or boost/buck converters, and/or the like). In some cases, the illuminators may be powered directly via batteries, when applicable.

In the current example, the controller 102 may be configured to modulate the output of each individual illuminator or light source in accordance with a dosage protocol for various operating modes either established prior to use or on-the-fly by the controller 102. The modulation may be controlled by the controller 102 by generating or switching the signals that controls the power stage circuitry or the output of the drivers 106 that power the illuminators or light sources. For example, the controller 102 may utilize a pulse width modulation technique which include some sort of feedback to the controller 102. For example, the feedback may include monitoring luminous output, junction temperature, metalclad board temperature, or the like. For example, as discussed herein, the irradiance levels outputted by each type of illuminator correlates to the injected current into the source and hence, the individual illuminator's irradiation output. The dosage delivered by the system 100 is also a function of the time at which the irradiance regime is sustained and the distance between the illuminator and the target being irradiated, say a region within certain physical constraints, a target body, a volume of air within a filtration system or the like. Hence, the close relationship between the location/distribution of the illuminators or light sources on the support structure 104 with respect to the target. It follows that this relationship is strongly influenced by the type of application or use of the system 100. The ability to control each type of illuminator independently allows for the embodiment to deliver distinctive and decoupled irradiance levels for each specific UV band and, accordingly, a dosage protocols regimen that is UV band specific.

In some cases, the controller 102 may utilize input provided by sensors 108 to adjust the operating mode and/or dosage protocols, by adjusting the irradiance levels of each type of illuminator in substantially real time based on various environmental factors. In these cases, the controller 102 may include a processor (e.g., microprocessor, microcontroller, DSP processor or the like) together with, for example, one or more machine learned models or networks, algorithms, hierarchies, thresholds, or the like. For instance, a linear regression technique that adjusts the dosage levels based on a direct feed of data generated by one or multiple sensors or a performance assessment algorithm, which makes use of a photodetector in order to adjust the irradiance levels of the different light source in order to compensate for their inherent degradation over time.

In some implementations, the controller 102 may receive sensor data from the sensors 108, input the sensor data into one or more machine learned model or otherwise process the sensor data to adjust or select the mode of operation or dosage protocols suitable for the current environmental conditions. The one or more machine learned model(s) may be generated using various machine learning techniques. In some cases, the machine learned models or networks may be trained using dosage protocols, environmental data associated with input and outputs to the environmental quality system 100 and the like. For example, the models may be generated using one or more neural network(s) and/or similar classification algorithms. A neural network may be a biologically inspired algorithm or technique which passes input data through a series of connected layers to produce an output or learned inference. Each layer in a neural network can also comprise another neural network or can comprise any number of layers (whether convolutional or not). As can be understood in the context of this disclosure, a neural network can utilize machine learning, which can refer to a broad class of such techniques in which an output is generated based on learned parameters. Artificial neural networks may be trained with evidence-based data that resulted from direct experimentation and/or scientific publications.

As an illustrative example, one or more neural network(s) may generate any number of learned inferences or heads from the captured sensor and/or image data. In some cases, the neural network may be a trained network architecture that is end-to-end. In one example, the machine learned models may include segmenting and/or classifying extracted deep convolutional features of the sensor and/or image data into semantic data. In some cases, appropriate truth outputs of the model in the form of semantic per-pixel classifications (e.g., vehicle identifier, container identifier, driver identifier, and the like).

Although discussed in the context of neural networks, any type of machine learning can be used consistent with this disclosure. For example, machine learning algorithms can include, but are not limited to, regression algorithms (e.g., ordinary least squares regression (OLSR), linear regression, logistic regression, stepwise regression, multivariate adaptive regression splines (MARS), locally estimated scatterplot smoothing (LOESS)), instance-based algorithms (e.g., ridge regression, least absolute shrinkage and selection operator (LASSO), elastic net, least-angle regression (LARS)), decisions tree algorithms (e.g., classification and regression tree (CART), iterative dichotomiser 3 (ID3), Chi-squared automatic interaction detection (CHAID), decision stump, conditional decision trees), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), association rule learning algorithms (e.g., perceptron, back-propagation, hopfield network, Radial Basis Function Network (RBFN)), deep learning algorithms (e.g., Deep Boltzmann Machine (DBM), Deep Belief Networks (DBN), Convolutional Neural Network (CNN), Stacked Auto-Encoders), Dimensionality Reduction Algorithms (e.g., Principal Component Analysis (PCA), Principal Component Regression (PCR), Partial Least Squares Regression (PLSR), Sammon Mapping, Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA)), Ensemble Algorithms (e.g., Boosting, Bootstrapped Aggregation (Bagging), AdaBoost, Stacked Generalization (blending), Gradient Boosting Machines (GBM), Gradient Boosted Regression Trees (GBRT), Random Forest), SVM (support vector machine), supervised learning, unsupervised learning, semi-supervised learning, etc. Additional examples of architectures include neural networks such as ResNet50, ResNet101, VGG, DenseNet, PointNet, and the like. In some cases, the system may also apply Gaussian blurs, Bayes Functions, color analyzing or processing techniques and/or a combination thereof.

In some examples, the sensors 108 may include various or multiple types of sensors to determine various environmental conditions. For example, the sensors 108 may include temperature sensors 108(A), VOC sensors 108(B), humidity sensors 108(C), $CO_2$ sensors 108(D), particulate matter sensors 108(E), as well as other sensors 108(F) that may be usable to determine one or more environmental conditions. In some specific examples, the particulate matter sensors may include particular matter counters PM1.0, PM2.5 and/or PM10.0 or similar to determine the presence and amount of respiratory virus and other pulmonary diseases in the environment. The $CO_2$ sensors 108(D) may be configured to generate data usable by the controller 102 to determine the presence and amount of anthropogenic activity. VOC sensors 108(B) may include total volatile organic counters and derivatives thereof to generate data usable to assess air quality levels, such as in indoor applications. The temperature sensors 108(A) and the humidity sensors 108(C) may generate data usable to determine an effectiveness of an UVC germicidal/disinfection system.

In some cases, the sensors 108 may also include an optical recognition sensor associated with a machine vision system (e.g., OpenCV and/or a pattern recognition algorithm such as You-Only-Look-Once (YOLO), or the like) to detect and quantify the number of individuals within a certain perimeter or environment and/or an ozone detector to generate data or signals that may be used to activate the UVC light sources or bands used to eliminate ozone presence from the mass of air being treated by the system 100. The system 100 may also utilize an occupancy sensor based on passive infrared (PIR), Microwave, or similar detection techniques to determine the presence and/or number of humans within certain spatial constraints or environment. In some cases, an ambience light level detector or sensors may be used to determine when certain operating modes are to be initiated (such as differing operational modes during the day and at night). In some cases, the sensors 108 may be positioned within a facility, location, or environment associated with the environmental quality system 100. In other cases, the sensors 108 may be coupled to the system 100 or the support structure 104, such as at an intake location.

In the current example, in contrast to conventional systems which are governed by pre-programmed runtime protocols or software routines, the system 100 operates in an autonomous fashion based on substantially real-time inputs and data that is used by the controller 102 together with machine learned models to generate or select operating modes and/or dosage protocols that are tailored for the specific environment and configured to extend the life-span of the UV illuminators (e.g., to turn off or reduce power provided by the drivers 106 when individual illuminators are unnecessary).

As some example operational modes, the system 100 may include initially begin operation in factory programmed mode and/or a user programed or initiated mode. The initial mode allows for a quick configuration of the embodiment as per applicable standards that specify dosage limits that are influenced by geometrical constraints such as room size, distance to reflective objects and other surfaces, and the like. The system 100 may also include a discovery mode that operates in a continuous mode within some pre-established limit that are part of a fuzzy logic algorithm. The system 100 may also include an autonomous mode that operates under a supervised learning set of rules dictated by machine learning model and/or networks in the form of classification and/or linear regression models. In the autonomous operation mode, the embodiment relies solely on the input data provided by the sensors 106 associated with the system 100 as well on the input provided by onboard timers, counters and other logic gate inputs such as interrupt functions.

In the current example, the controller 102 may be communicatively coupled to one or more communication interface(s) 110. The one or more communication interfaces(s) 110 may enable communication between the system 100 and one or more other local or remote computing device(s) or remote services, such as remote sensors 108, remote machine learning systems, remote processing systems, or the like. The communications interfaces(s) 110 may enable Wi-Fi-based communication such as via frequencies defined by the IEEE 802.11 standards, short range wireless frequencies such as Bluetooth, cellular communication (e.g., 2G, 3G, 4G, 4G LTE, 5G, etc.), satellite communication, dedicated short-range communications (DSRC), or any suitable wired or wireless communications protocol that enables the respective computing device to interface with the other computing device(s).

Figure 2:
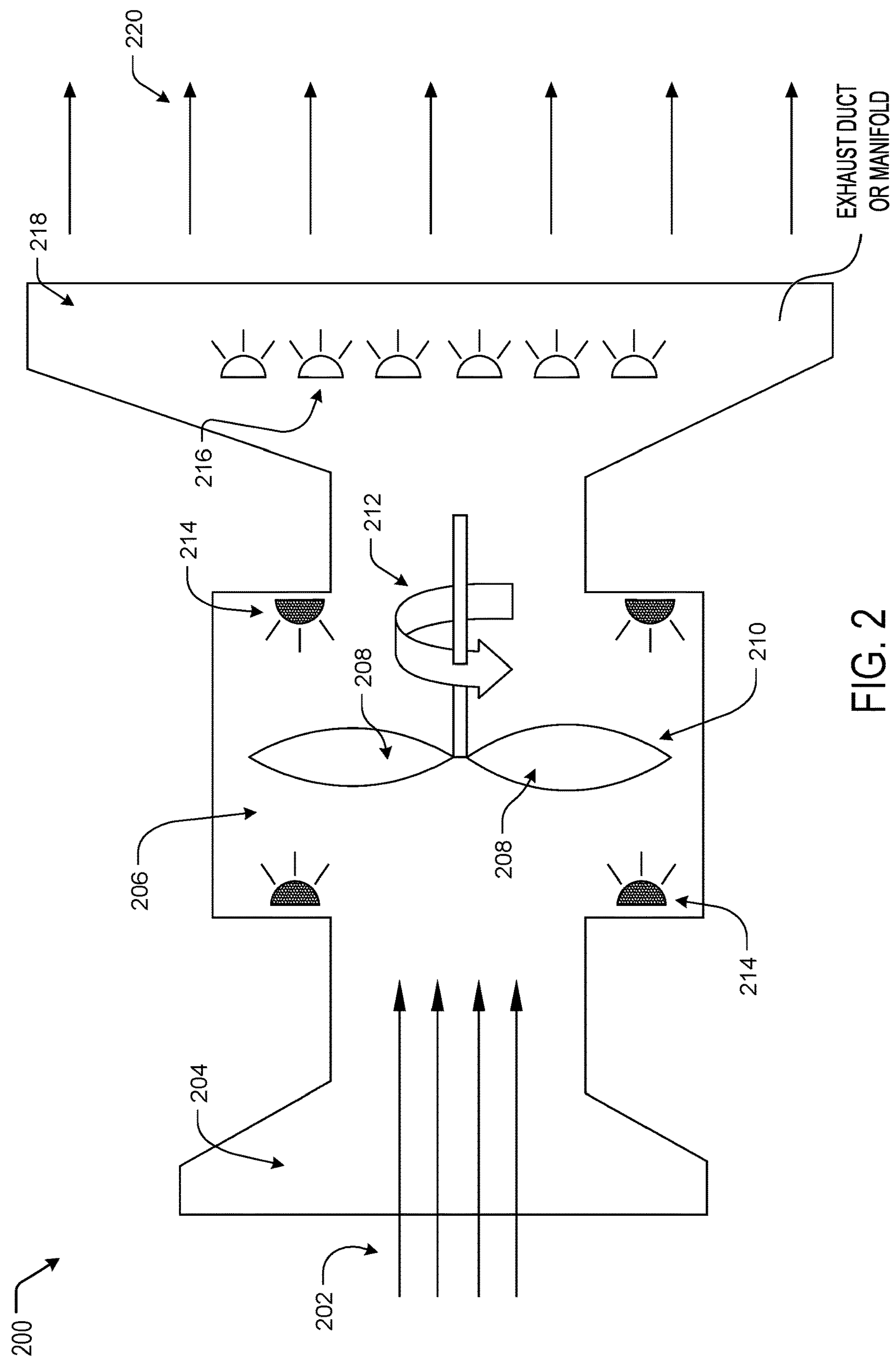
FIG. 2 is an example pictorial diagram of an environmental quality system according to some implementations.

FIG. 2 is an example pictorial diagram of an environmental quality system 200 according to some implementations. In the current example, the system 200 may receive air, generally indicated by arrows 202, from an environment via an intake duct or manifold 204. The air 202 from the environment may enter a chamber 206 including a propeller or impeller 208 of a fan 210. The impeller 208 may be coated with a nanostructured ceramic (such as titanium dioxide). The fan 210 may cause the air 202 to flow within the chamber 206 in a circular motion for a period of time, generally indicated by arrow 212.

As the air 202 flows within the chamber 206, one or more illuminators 214 may irradiate the air 202 as well as any anthropogenic compounds, contaminants or other chemical compounds present together within the air 202. For example, the illuminators 214 may be wide angle UVA light sources (such as LEDs) to increase the irradiance coverage to the impeller 208 to assist with the PCO processes that apply to the air 202 (or water in other applications) by modulating distinctive irradiation spanning from the UVA bands through, for example, the UVC bands. In some cases, the nanostructured ceramic coating may act as a catalyst that causes a reaction with UVC irradiation and converts the anthropogenic components, contaminants or other chemical compounds into water, carbon dioxide, and/or other harmless detritus.

As the air 202 exits the chamber 206, the air may be irradiated again by the illuminators 216 positioned within the exhaust manifold 218. The illuminators 216 may be a narrow angle UVC light source to project the irradiance far into the free space after the air 202 exits the exhaust manifold 218, generally indicated by arrows 220. In this manner, the air 202 may be irradiated multiple times to provide for improved air quality output.

Figure 3:
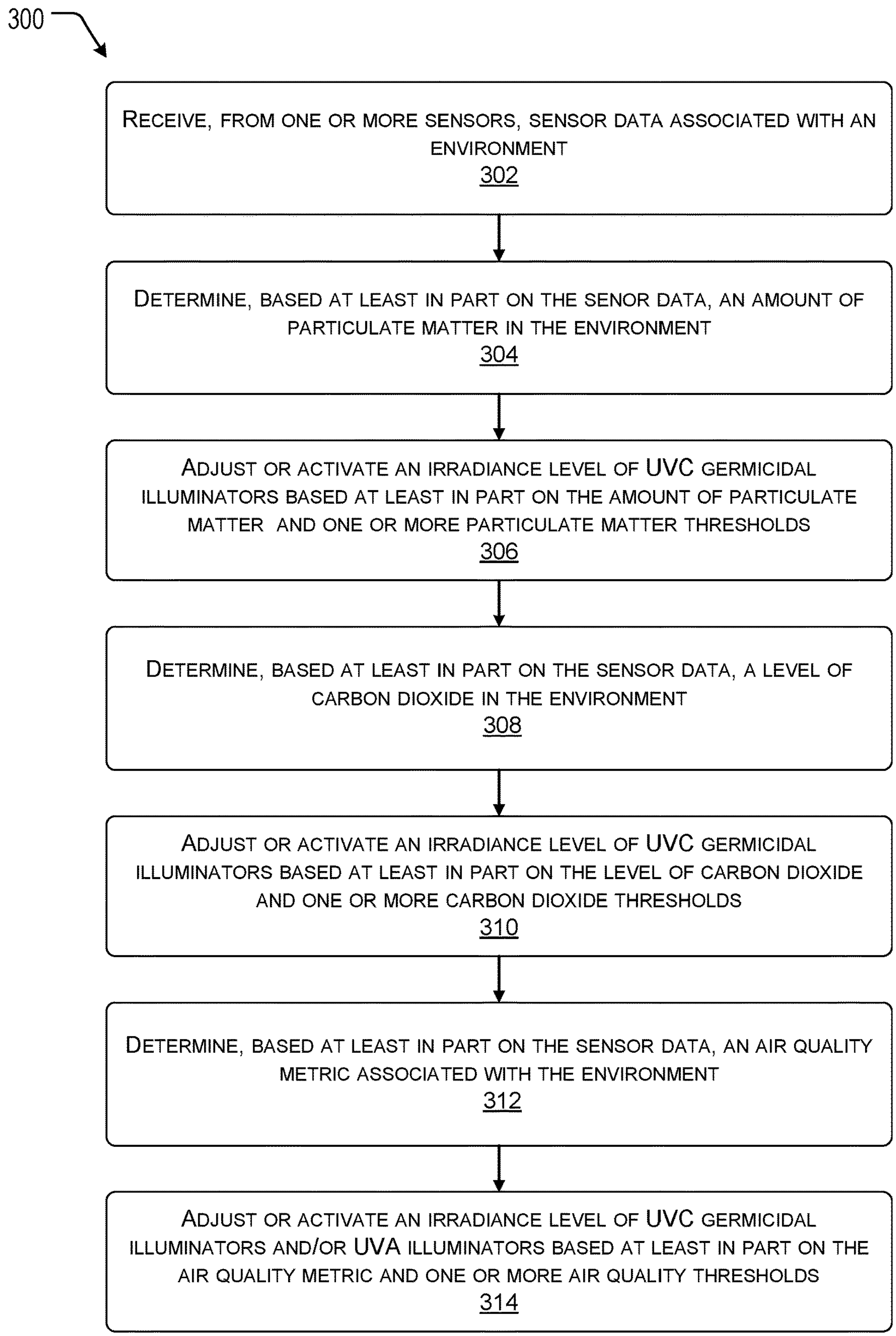
FIG. 3 is a flow diagram illustrating an example process associated with an environmental quality system according to some implementations.
Figure 4:
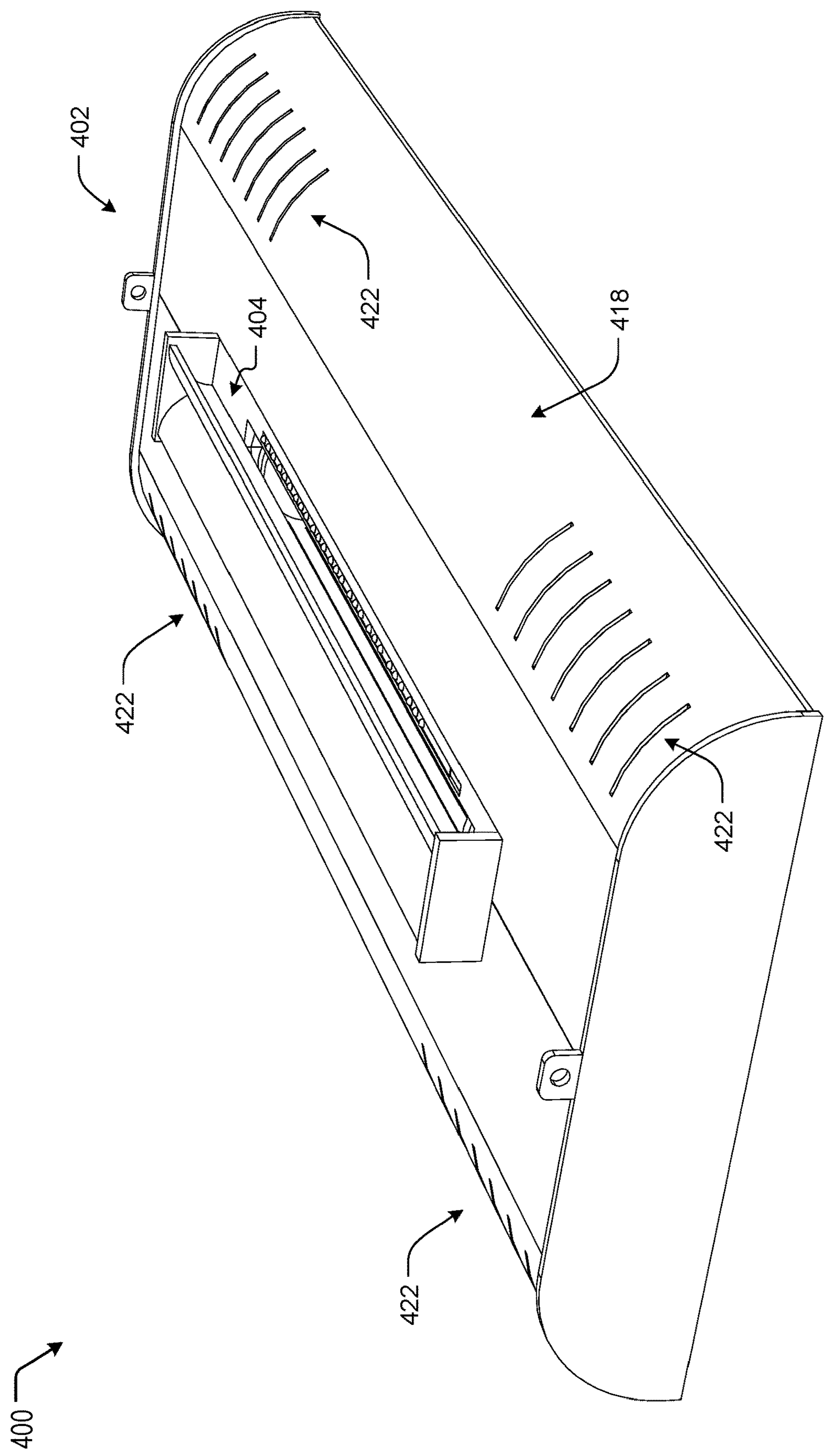
FIG. 4 illustrates an example perspective pictorial diagram from the top of a first environmental quality system according to some implementations.
Figure 5:
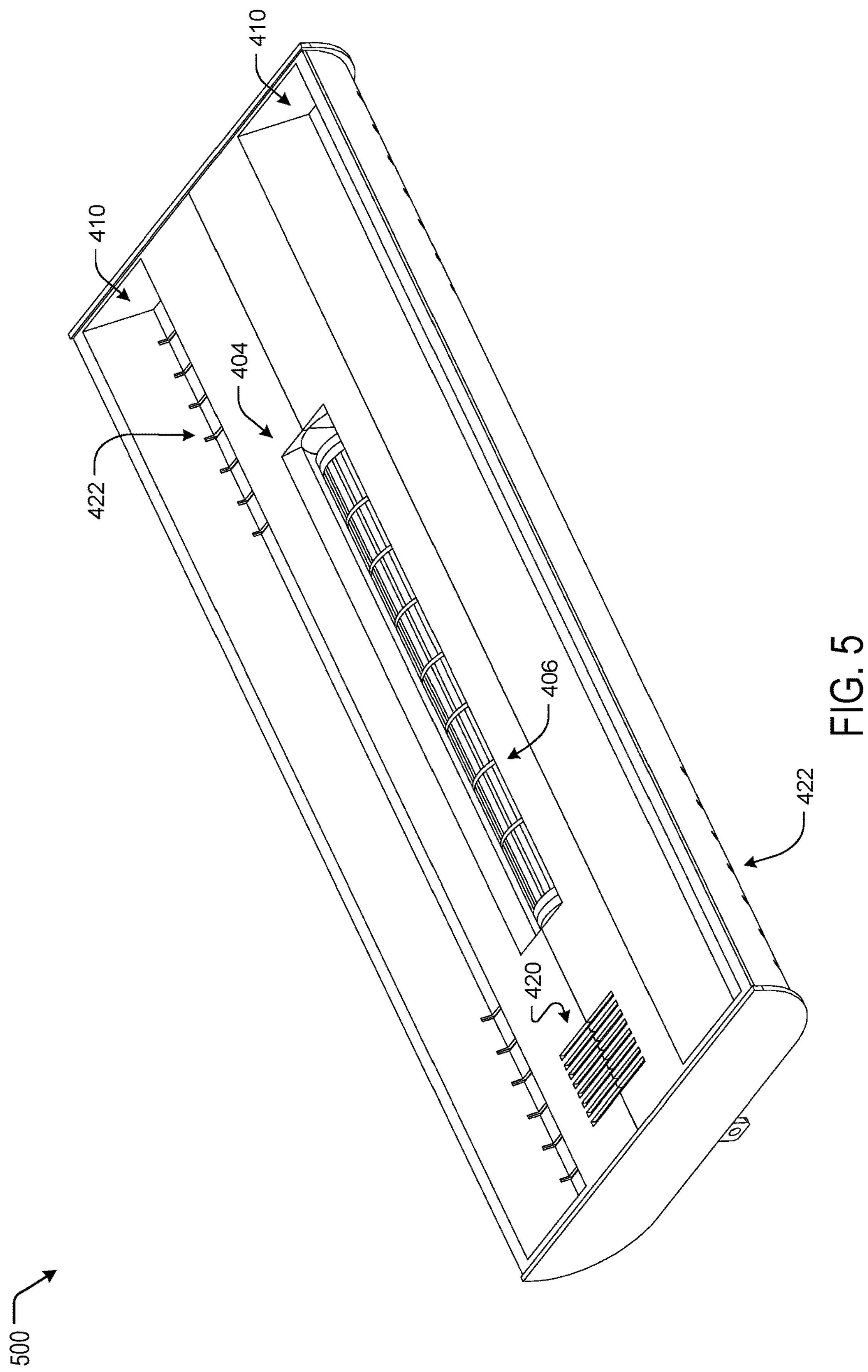
FIG. 5 illustrates an example perspective pictorial diagram from the bottom of the first environmental quality system of FIG. 4 according to some implementations.
Figure 6:
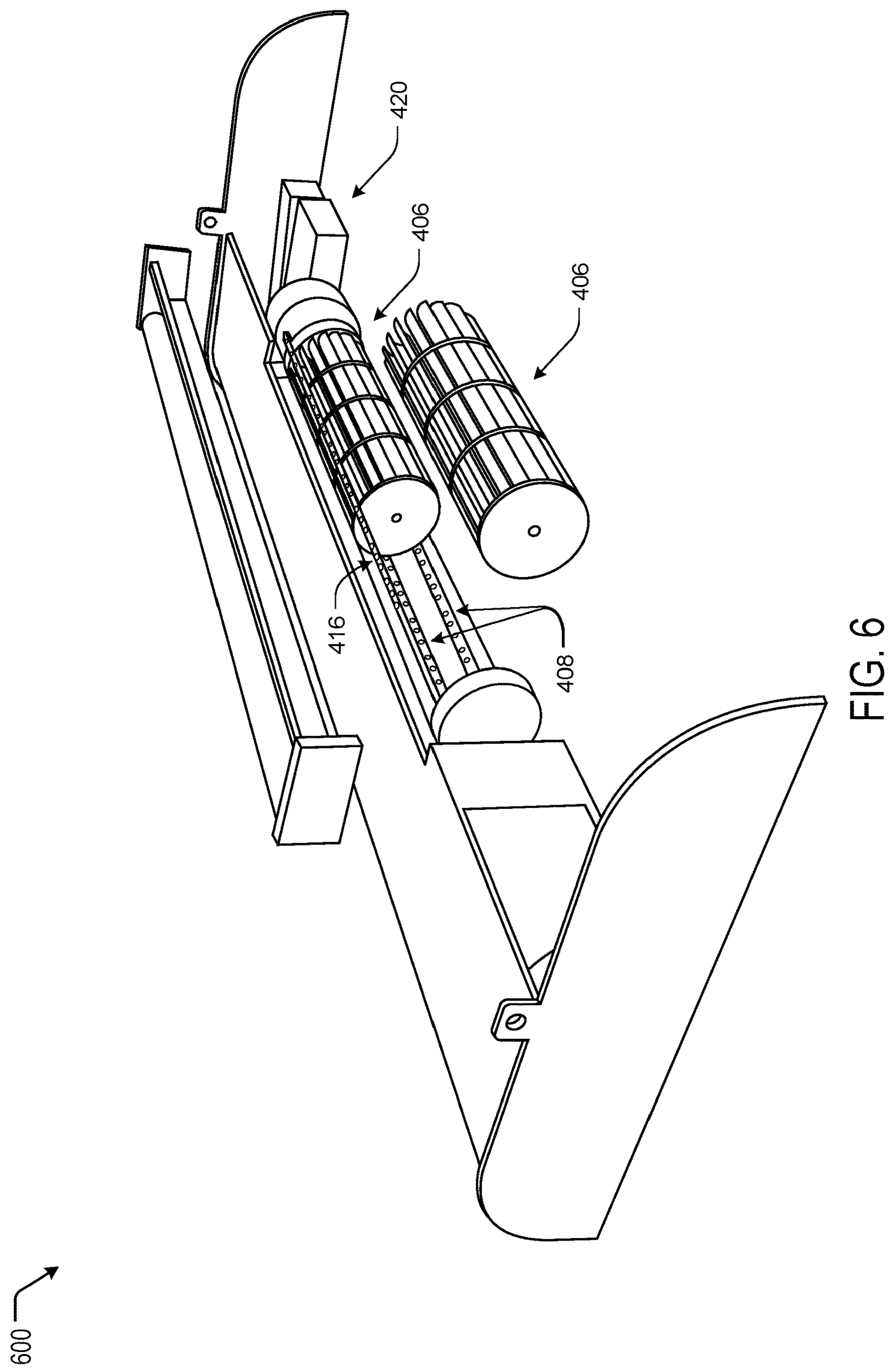
FIG. 6 illustrates an example perspective pictorial diagram from the top of the first environmental quality system of FIG. 4 with a cover removed according to some implementations.
Figure 7:
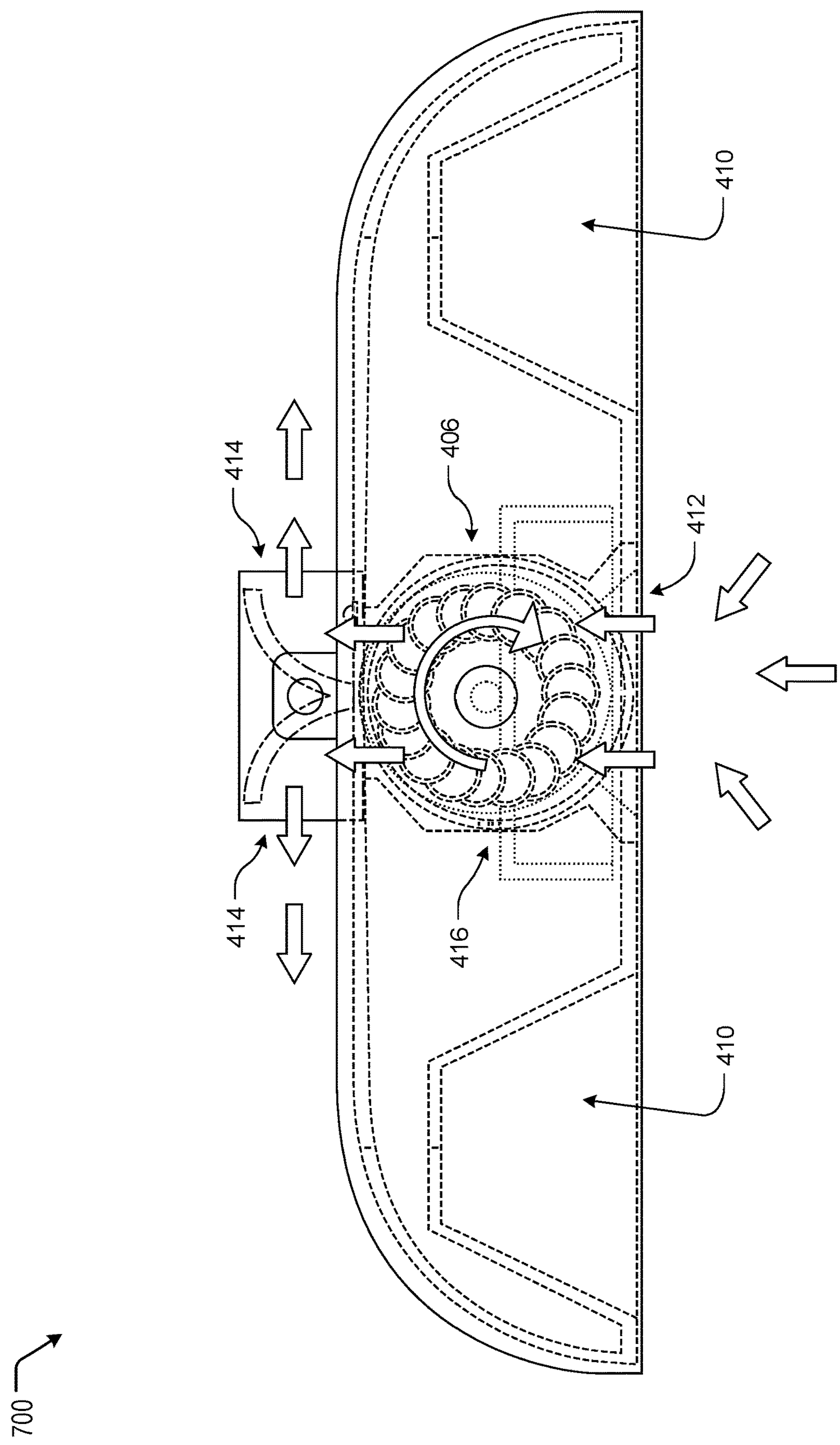
FIG. 7 illustrates an example cross sectional diagram from the side of the first environmental quality system of FIG. 4 according to some implementations.
Figure 8:
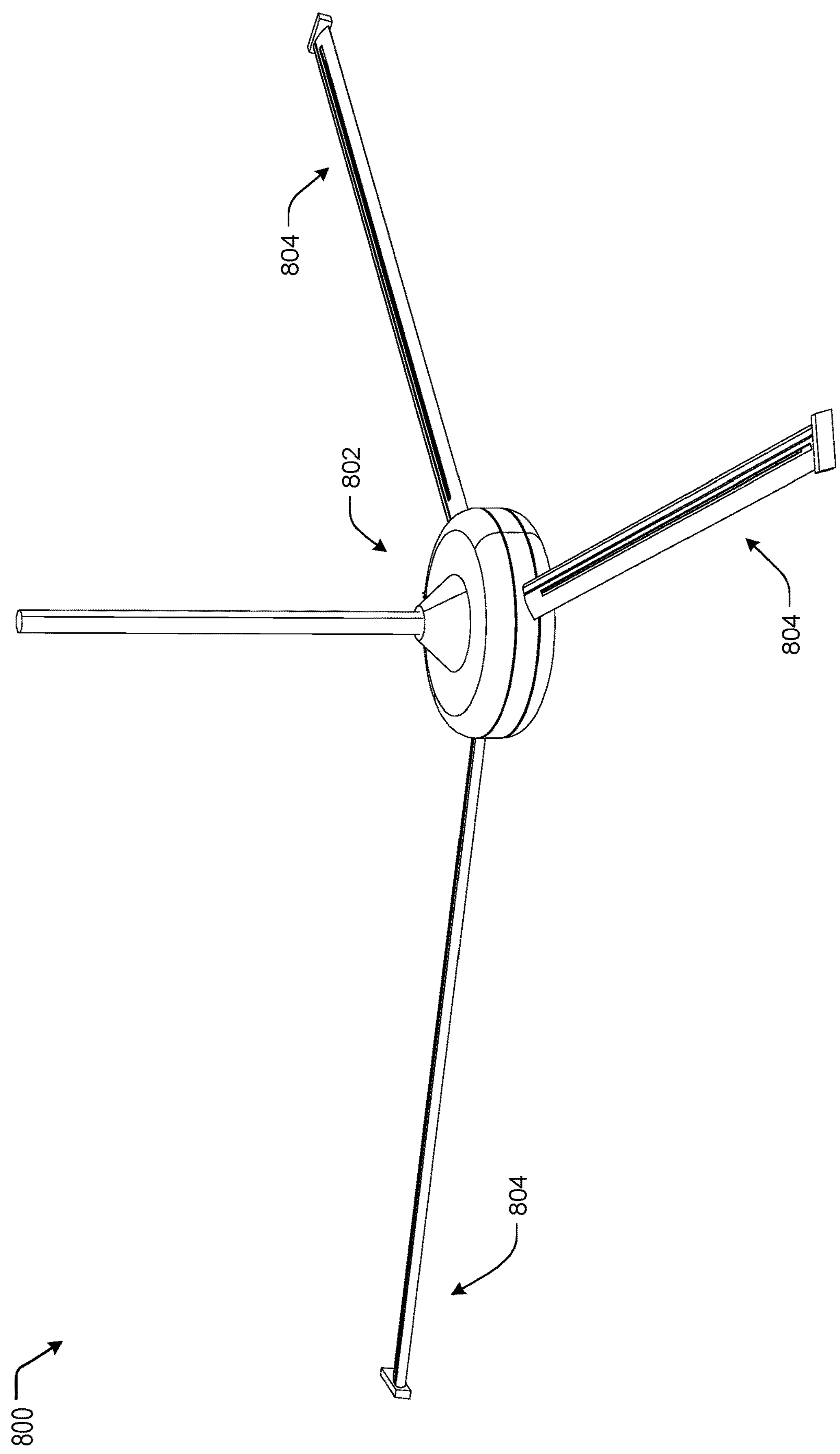
FIG. 8 illustrates an example perspective pictorial diagram from the top of a second environmental quality system according to some implementations.
Figure 9:
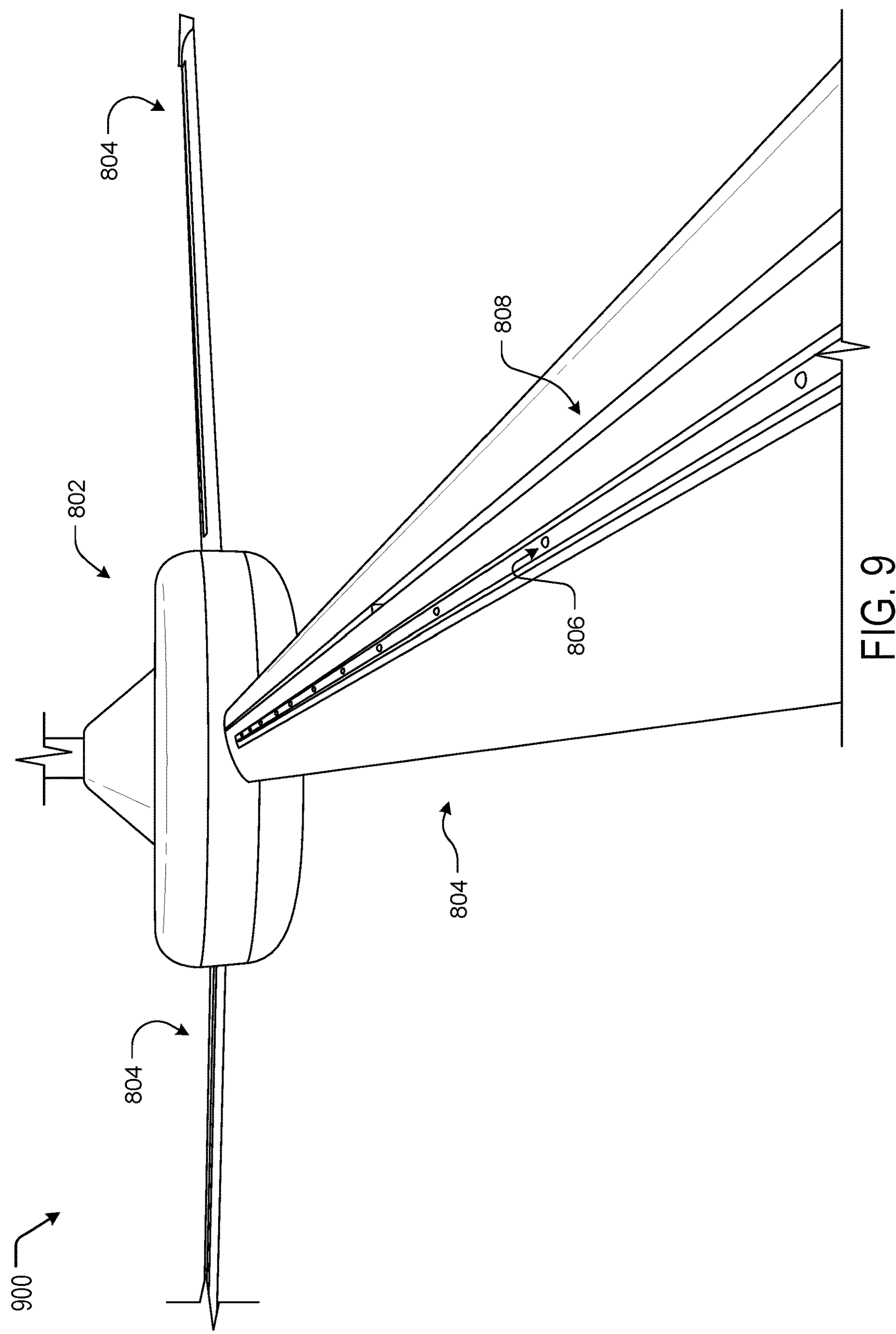
FIG. 9 illustrates an example side view of the second environmental quality system of FIG. 8 according to some implementations.
Figure 10:
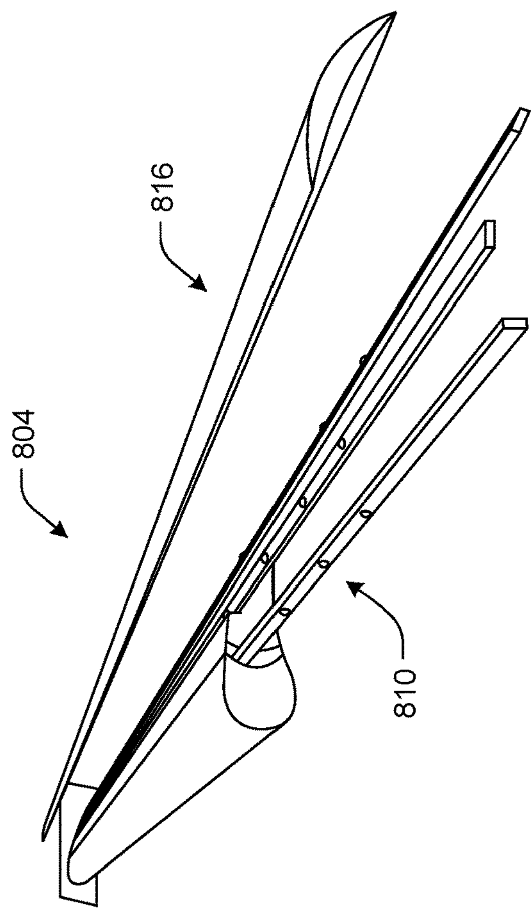
FIG. 10 illustrates an example exploded view of a blade of the second environmental quality system of FIG. 8 according to some implementations.
Figure 10:
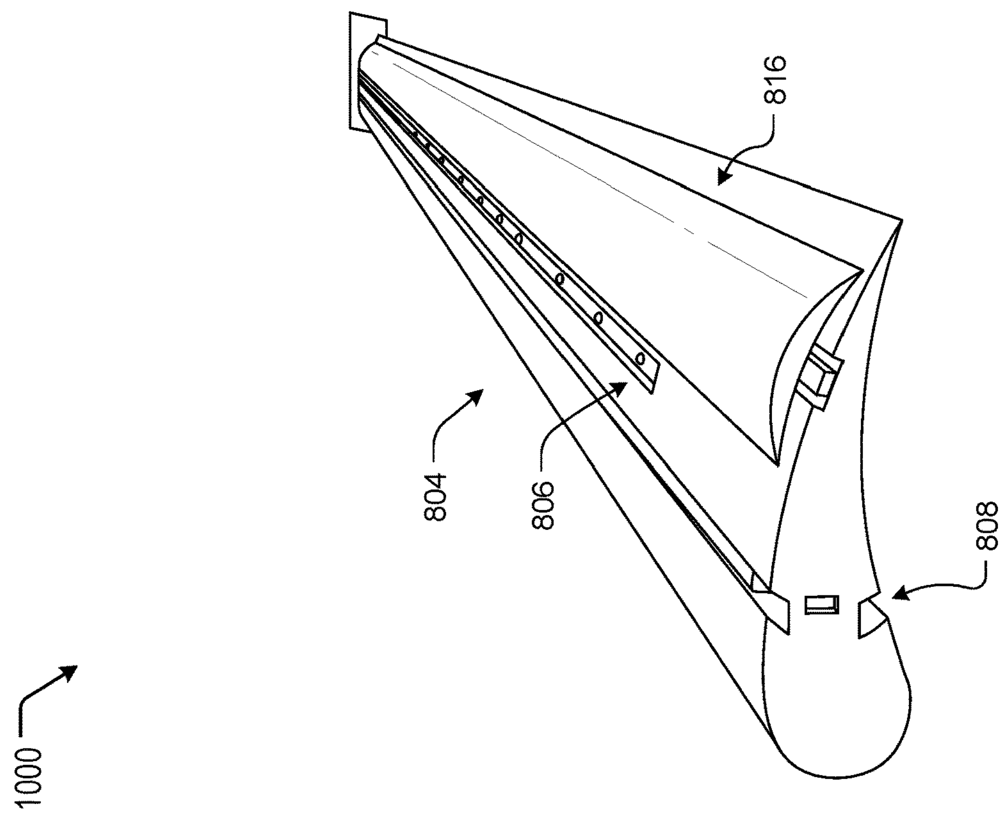
Figure 11:
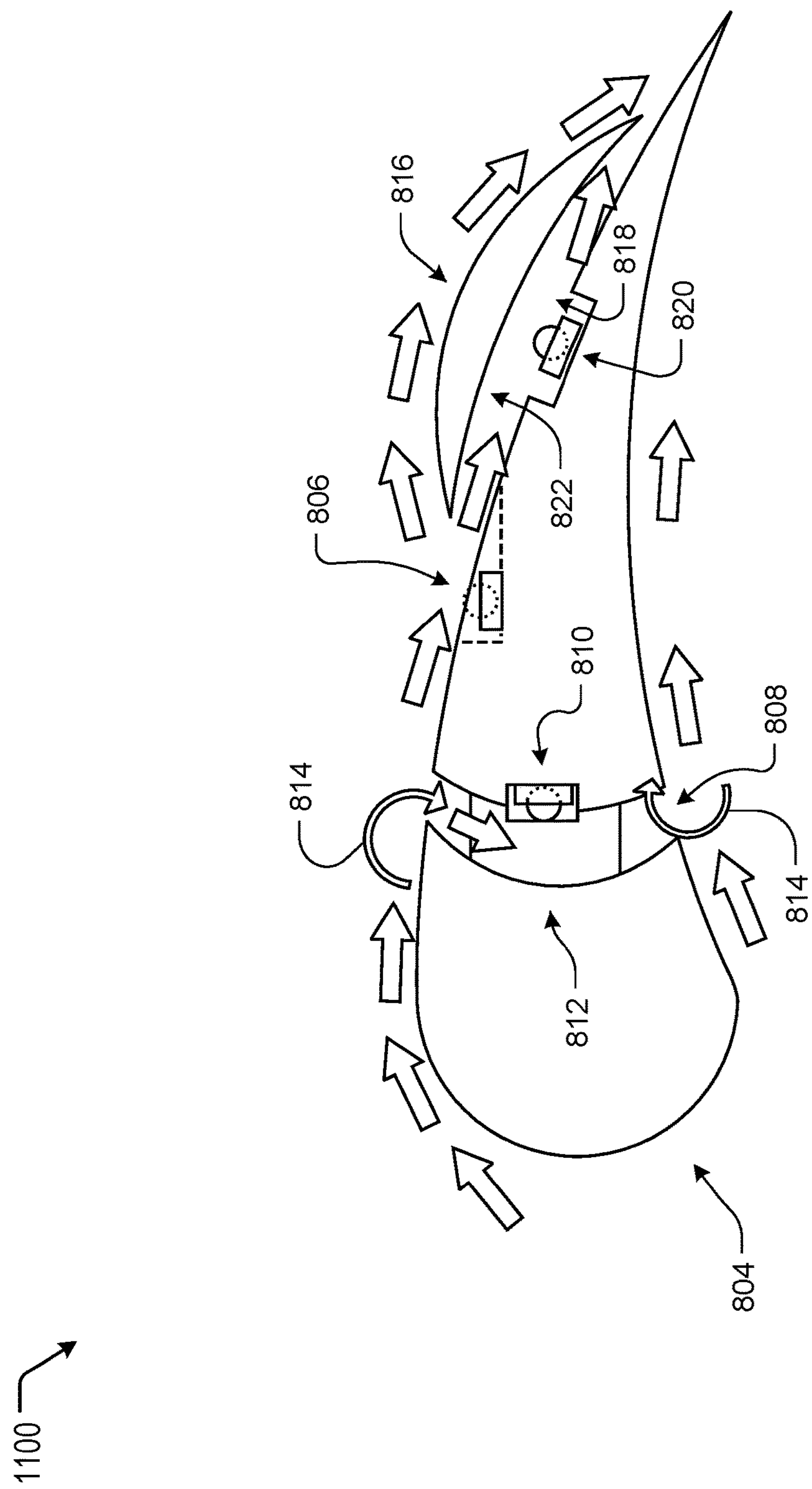
FIG. 11 illustrates an example cross sectional diagram of the blade of the second environmental quality system of FIG. 8 according to some implementations.
Figure 12:
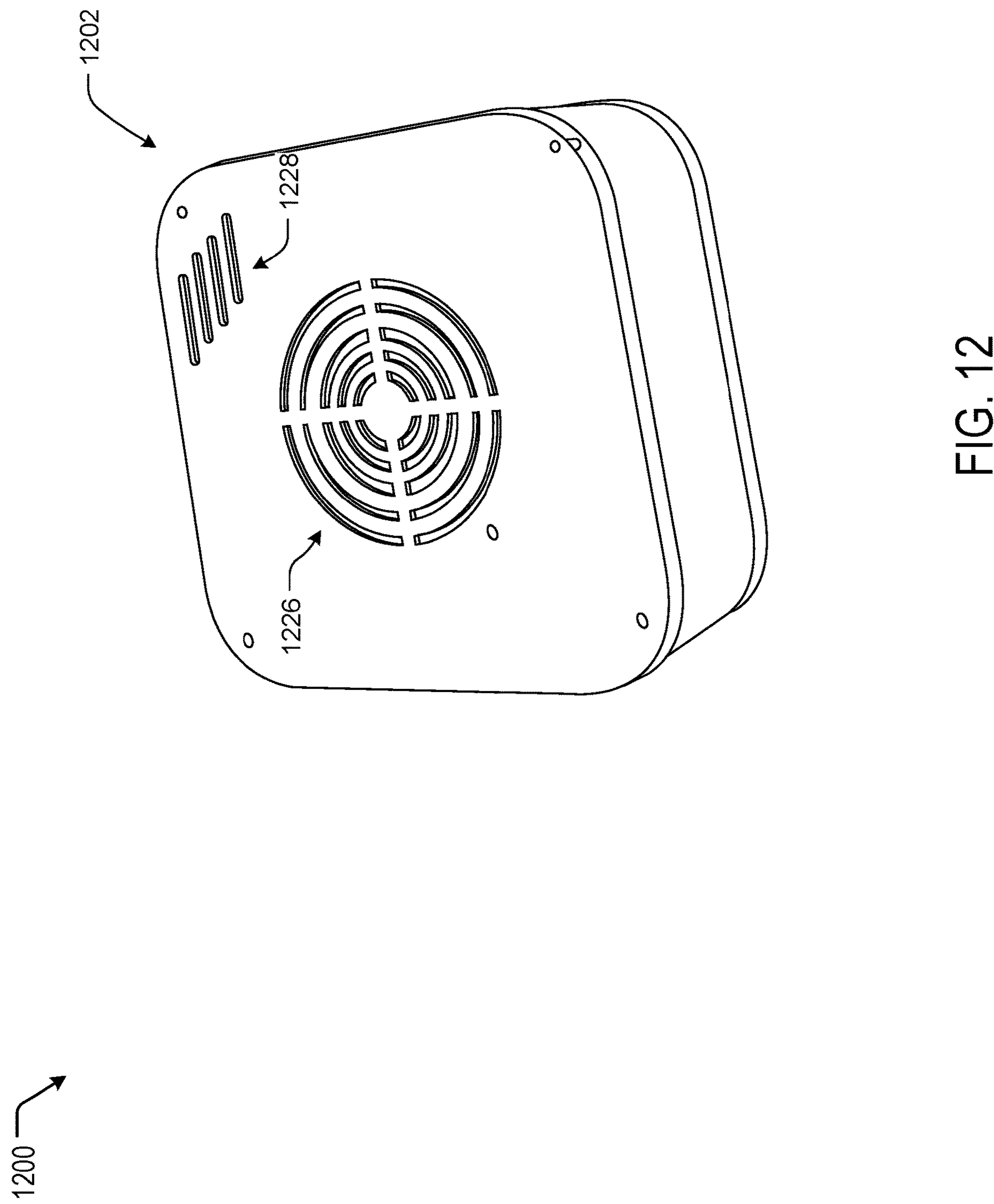
FIG. 12 illustrates example perspective pictorial diagrams from the top of a third environmental quality system according to some implementations.
Figure 13:
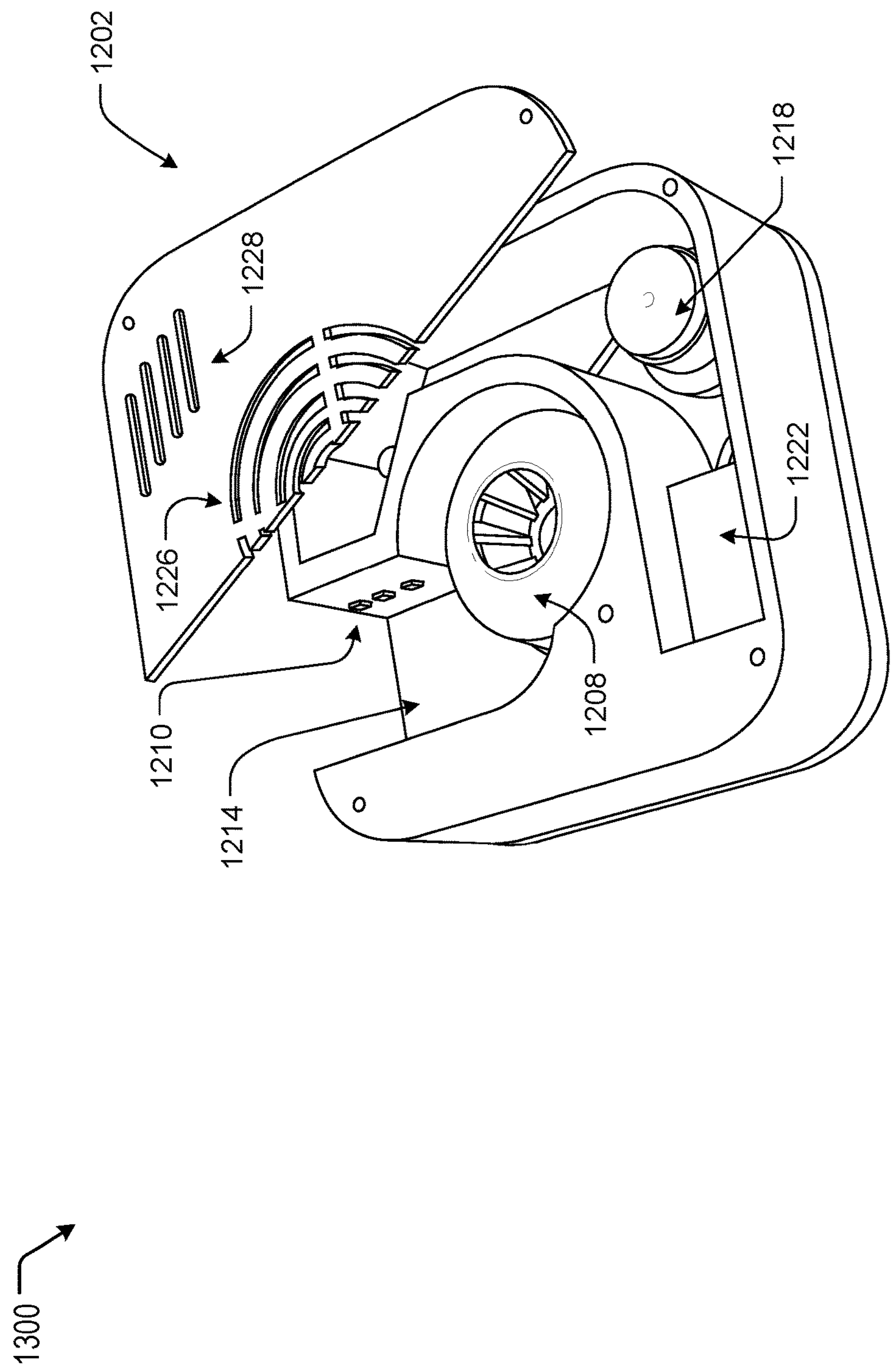
FIG. 13 illustrates an example view of the third environmental quality system of FIG. 12 with a cover removed according to some implementations.
Figure 14:
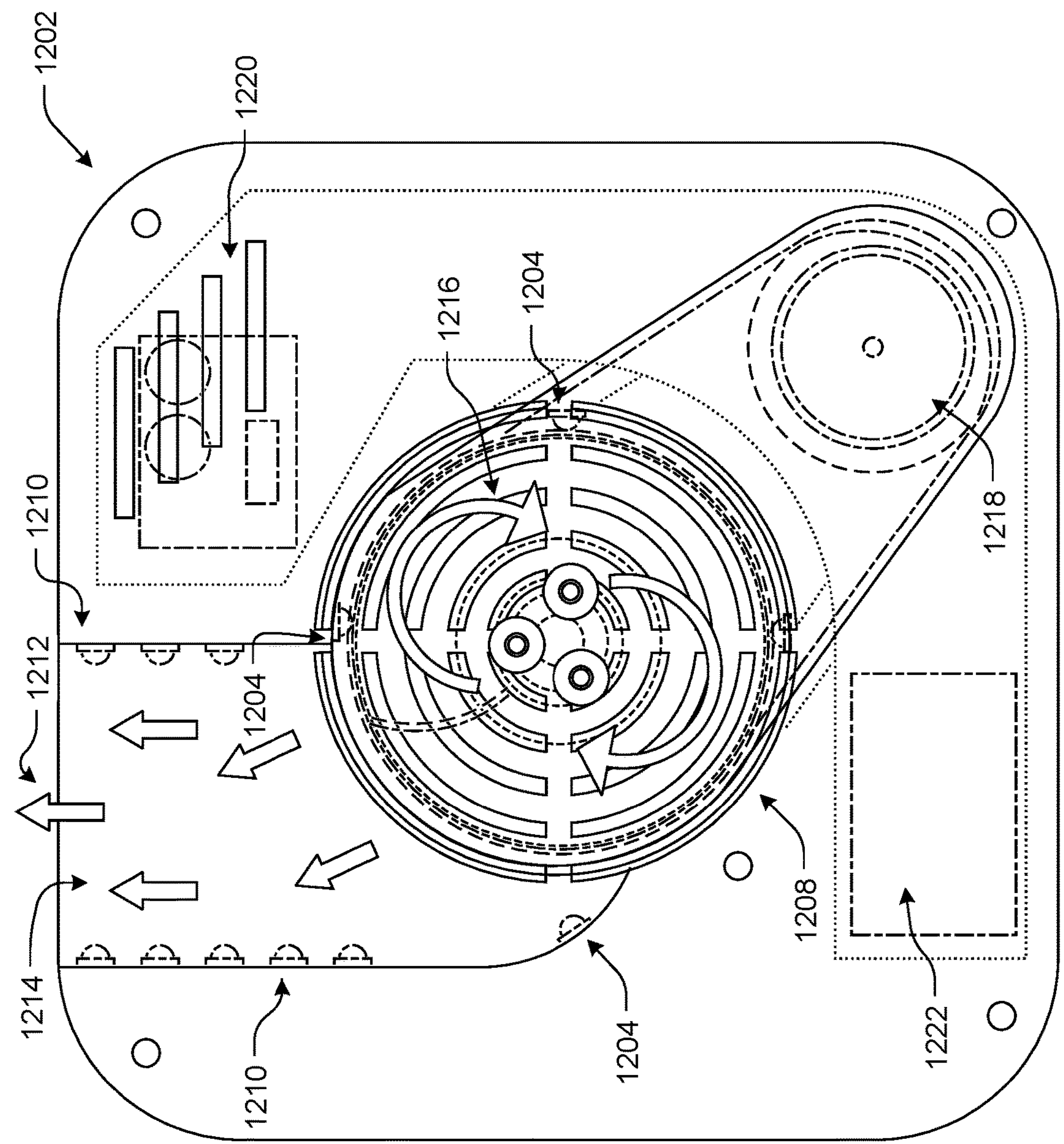
FIG. 14 illustrates an example cross sectional diagram of the third environmental quality system of FIG. 12 according to some implementations.
Figure 15:
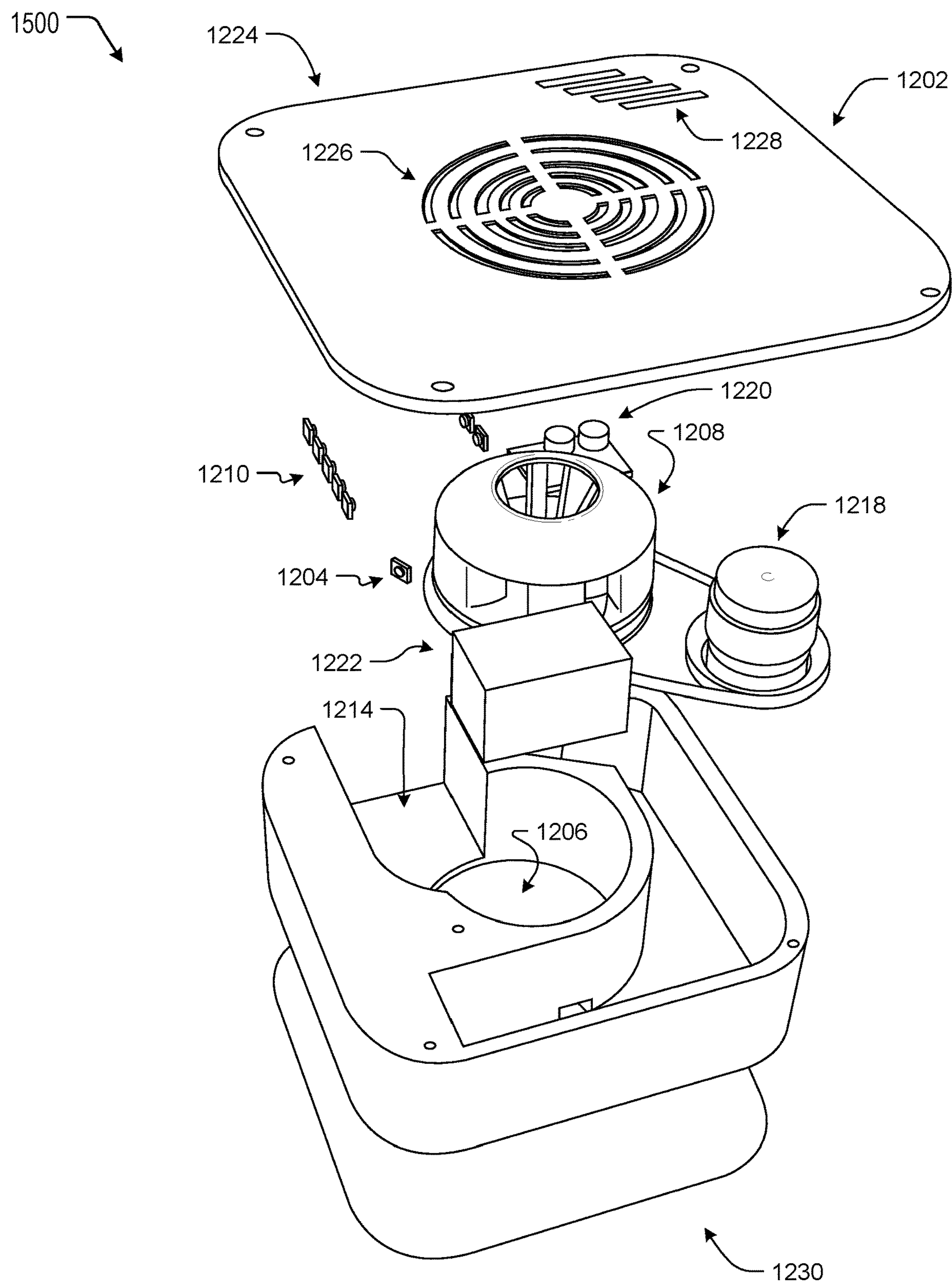
FIG. 15 illustrates an example exploded view of a blade of the third environmental quality system of FIG. 12 according to some implementations.
Figure 16:
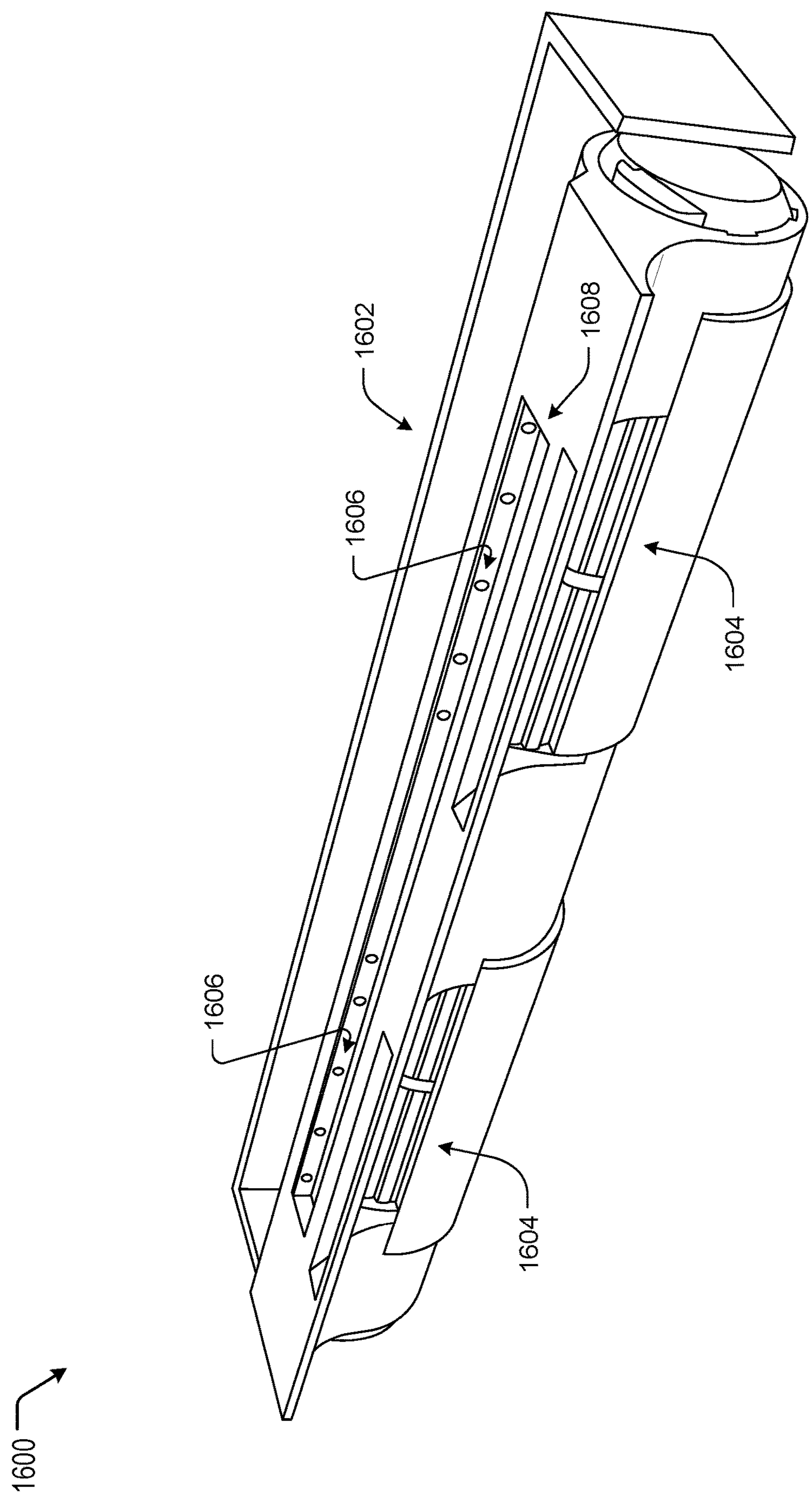
FIG. 16 illustrates example perspective pictorial diagrams from the top of a fourth environmental quality system according to some implementations.
Figure 17:
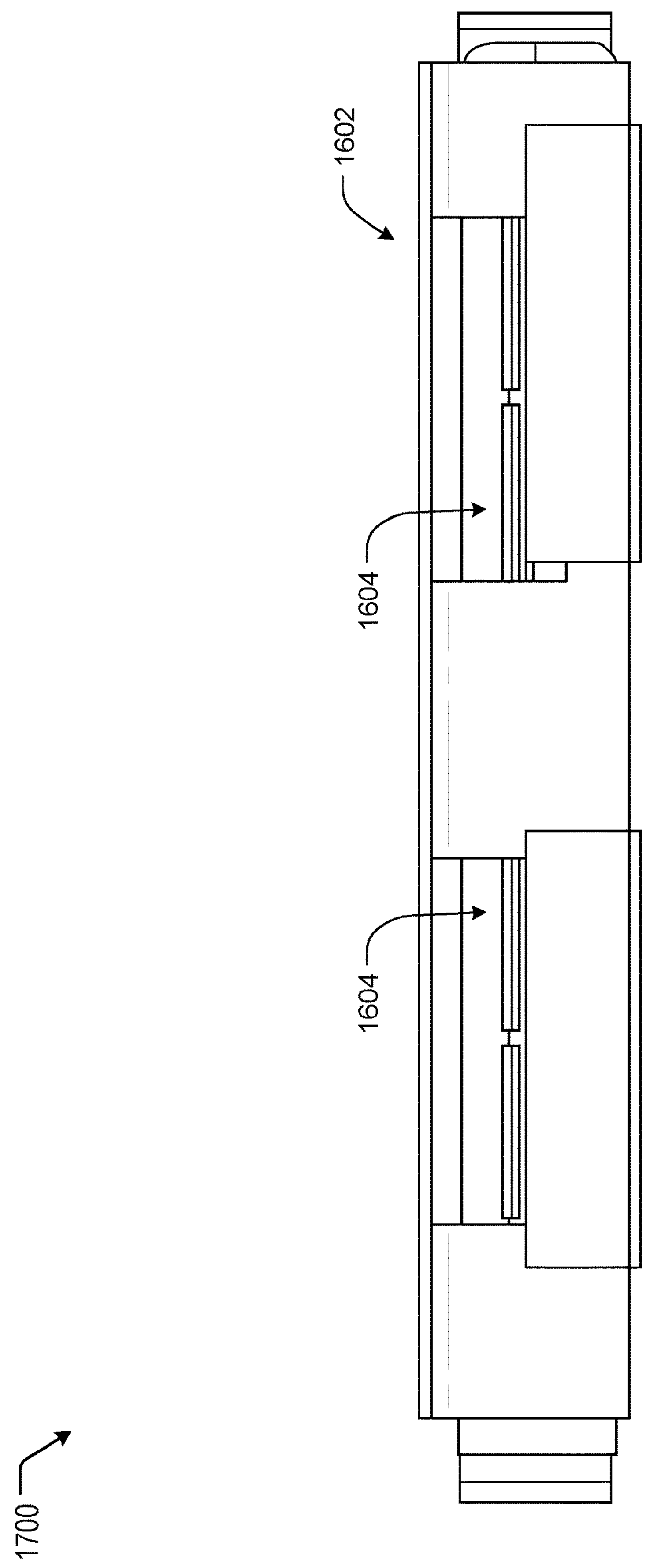
FIG. 17 illustrates an example front view of the fourth environmental quality system of FIG. 16 according to some implementations.
Figure 18:
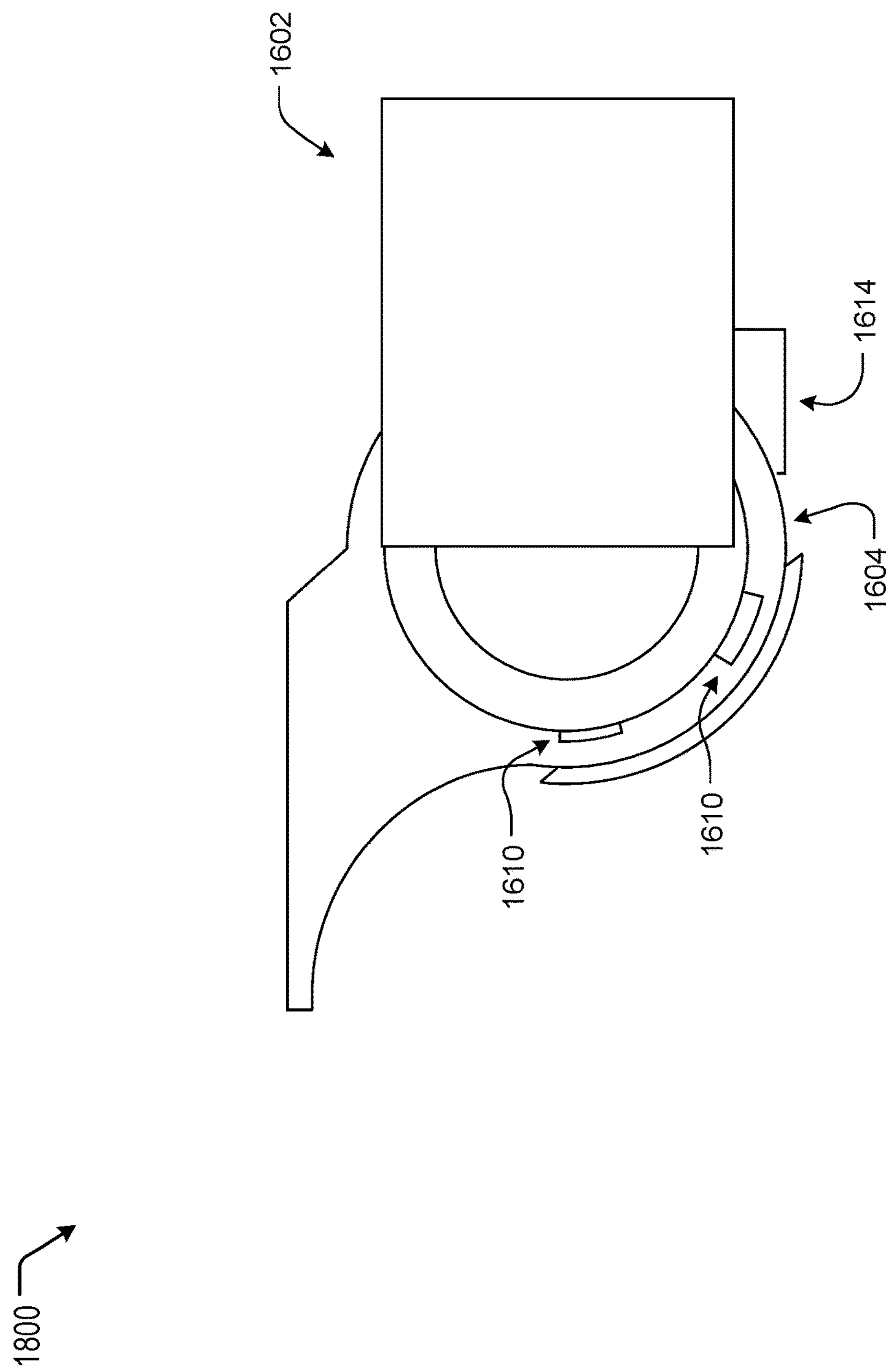
FIG. 18 illustrates an example side view of the fourth environmental quality system of FIG. 16 according to some implementations.
Figure 19:
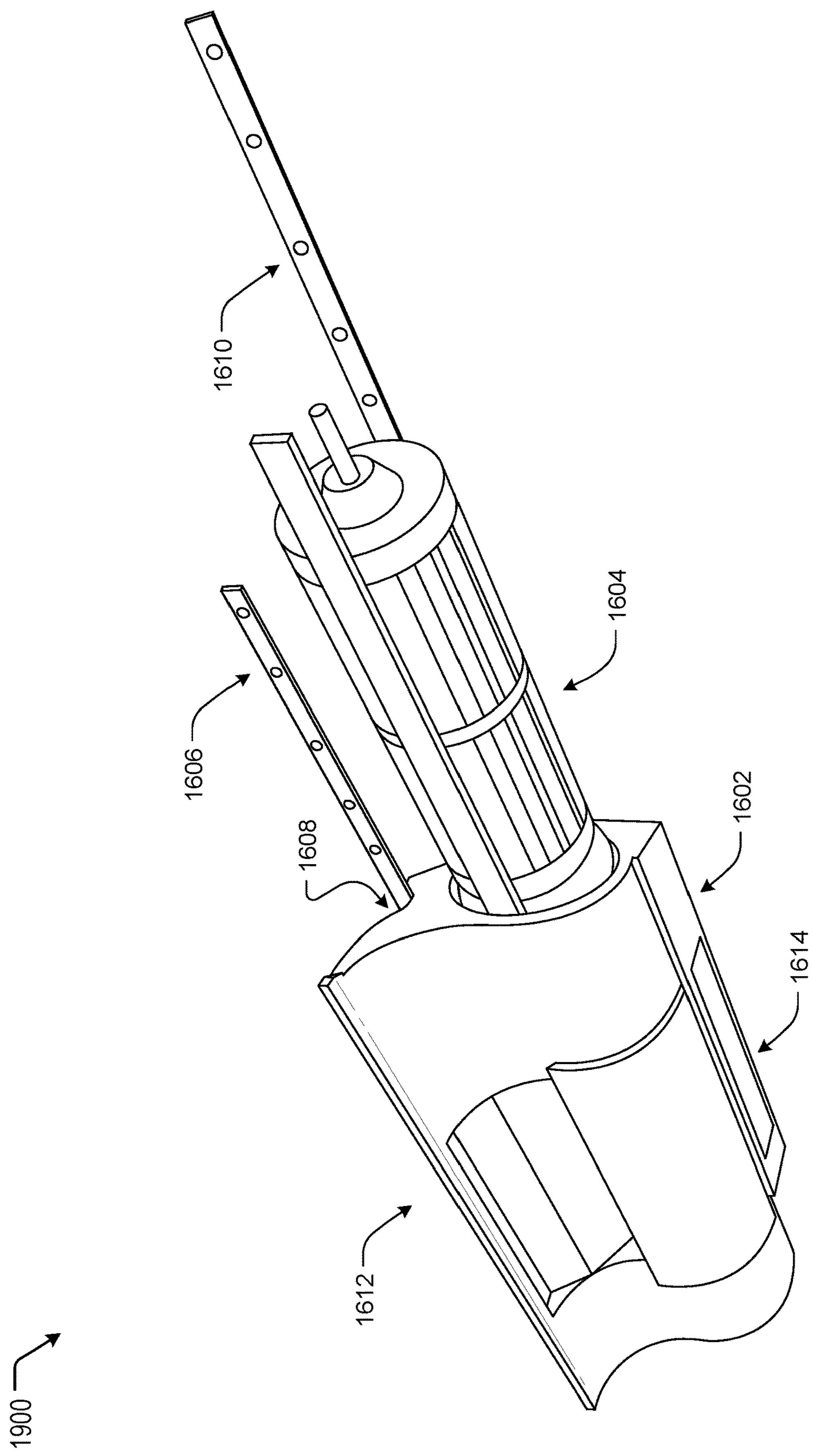
FIG. 19 illustrates an example exploded view of the fourth environmental quality system of FIG. 16 according to some implementations.
Figure 20:
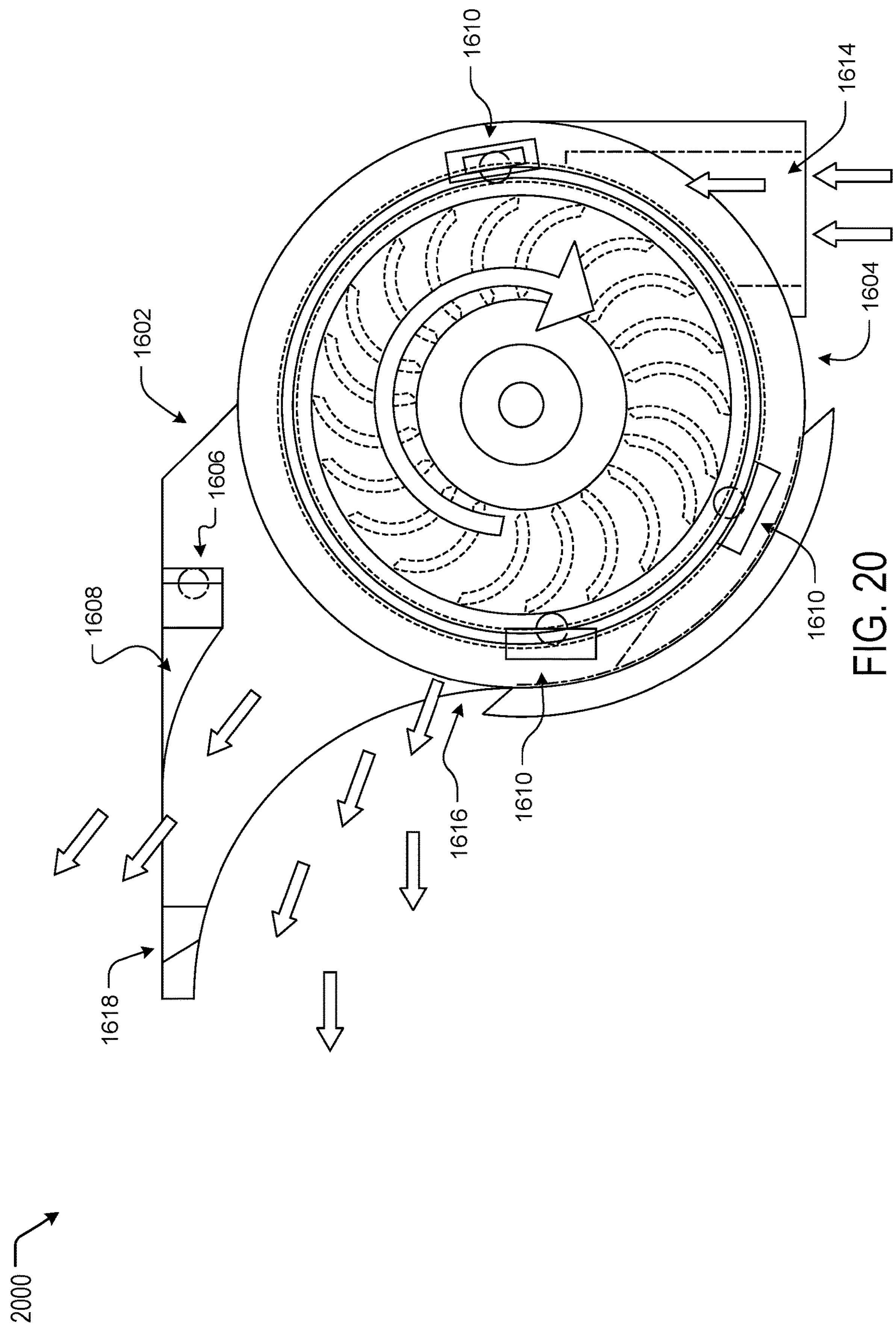
FIG. 20 illustrates an example cross sectional view of the fourth environmental quality system of FIG. 16 according to some implementations.

FIG. 3 is a flow diagram illustrating an example process associated with the environmental quality system discussed herein. The processes are illustrated as a collection of blocks in a logical flow diagram, which represent a sequence of operations, some or all of which can be implemented in hardware, software, or a combination thereof. In the context of software, the blocks represent computer-executable instructions stored on one or more computer-readable media that, which when executed by one or more processor(s), perform the recited operations. Generally, computer-executable instructions include routines, programs, objects, components, encryption, deciphering, compressing, recording, data structures and the like that perform particular functions or implement particular abstract data types.

The order in which the operations are described should not be construed as a limitation. Any number of the described blocks can be combined in any order and/or in parallel to implement the processes, or alternative processes, and not all of the blocks need be executed. For discussion purposes, the processes herein are described with reference to the frameworks, architectures and environments described in the examples herein, although the processes may be implemented in a wide variety of other frameworks, architectures or environments.

FIG. 3 is a flow diagram illustrating an example process 300 associated with an environmental quality system, such as the environmental quality system of FIGS. 1 and 2, according to some implementations. As discussed above, the environmental quality system may activate, deactivate, or adjust an irradiation level of one or more illuminations (e.g., UVA and/or UVC light sources) based on received sensor data, outputs of one or more machine learned models and/or networks, one or more thresholds (such as performance level indexes or weighted solutions), a combination thereof, or the like.

At 302, the environmental quality system may receive, from one or more sensors, sensor data associated with an environment (such as a building, vehicle, or the like). In some examples, the sensors may include temperature sensors, humidity sensors, volatile organic compound (VOC) sensors, carbon dioxide sensors, particulate matter sensors, other air quality sensors, or the like.

At 304, the environmental quality system may determine, based at least in part on the sensor data, an amount of particular matter in the environment. For example, the system may process the sensor data from one or more particulate matter sensors to determine an amount.

At 306, the environmental quality system may adjust or activate an irradiance level of UVC germicidal illuminators based at least in part on the amount of particulate matter and one or more particulate matter thresholds. In some cases, the system may input the sensor data into one or more machine learned models and receive the irradiance level (and/or a period of time to remain active for) as an output of the model. In other cases, the system may compare the amount of particulate matter to one or more performance levels or index-weighted heuristics (such as determined via testing, historical data or results, or via one more machine learned models and/or networks, a combination thereof, or the like).

At 308, the environmental quality system may determine, based at least in part on the sensor data, a level of $CO_2$ in the environment. For example, the system may process the sensor data from one or more $CO_2$ sensors to determine the level.

At 310, the environmental quality system may adjust or activate an irradiance level of UVC germicidal illuminators based at least in part on the level of $CO_2$ and one or more $CO_2$ thresholds. In some cases, the system may input the sensor data into one or more machine learned models and receive the irradiance level (and/or a period of time to active for) as an output of the model. In other cases, the system may compare the level of $CO_2$ (and/or other gases such as $O_3$, CO, $SO_2$, $NH_3$, presence of heavy metals including lead) to one or more performance levels or index-weighted heuristics (such as determined via testing, historical data or results, or via one more machine learned models and/or networks, a combination thereof, or the like).

At 312, the environmental quality system may determine, based at least in part on the sensor data, an air quality metric associated with the environment. For example, the system may process the sensor data from a combination of sensors (such as temperature, humidity, and the like) to determine the air quality metric.

At 314, the environmental quality system may adjust or activate an irradiance level of UVC germicidal illuminators and/or UVA illuminators (and perhaps the air or water flow rate into the chamber) based at least in part on the air or water quality metric and one or more air quality thresholds. In some cases, the system may input the sensor data into one or more machine learned models and receive the irradiance level (and/or a period of time to active for) as an output of the model. In other cases, the system may compare the air or water quality metric to one or more performance levels or index-weighted heuristics (such as determined via testing, historical data or results, or via one more machine learned models and/or networks, a combination thereof, or the like).

FIGS. 4-7 illustrates example 400-700 of a first environmental quality system 402 according to some implementations. In the current examples 400-700, the environmental quality system 402 is a general-purpose lighting system that integrates visible spectrum illuminator or light sources, via for example light sockets 410, that may be used for general purpose lighting while integrating a motorized forced-air mechanism 404 based on a cross-flow impeller 406. This impeller 406 may be coated with a layer of a photocatalytic oxidizing ceramic with specialized microstructure exhibiting a desired PCO performance within the spectral emission of the illuminator 408 associated with the mechanism 404.

In the examples 400-700, the illuminators 408 may be a series of LEDs sources tuned to a desired PCO performance of the ceramic coating and oriented towards the center axis of the impeller 406. A separated set of illuminators 416 (e.g., germicidal LEDs) are oriented upwards such to increase a dwell time between the airflow propelled by the impeller 406 and the germicidal light sources. By increasing the dwell time, a desired dosage of germicidal UV irradiance may be applied to the circulating air within the system 402. Moreover, a controller can also exert control or otherwise adjust the rotational speed of the impeller 406 and the intensity of the illuminators 408 to achieve the desired dosage. In some cases, the illuminators 408 (e.g., the germicidal LEDs) may be positioned upward with respect to the system 402, generally indicated as 416.

As discussed herein, the system 402 may serve a dual purpose. For instance, the system 402 may operate as an air purifier by mineralizing organic compounds via the photocatalytic oxidizing surface irradiated with specialized illuminators (e.g., UVA, UVC, and/or combination thereof, or the like) and also as an air disinfection device by irradiating the treated air while in the PCO chamber or while being exhausted using a light source or second illuminators tuned within the germicidal spectrum (e.g., far-UV and UVC light sources).

In some cases, the impeller 406 may be designed such that the impeller 406 may be replaced in-situ with ease. The replacement in-situ allows for the selection of an impeller 406 with the proper ceramic coating for the desired application or purpose of the system 402. For instance, in a smell reduction strategy, an impeller 406 coated with silver doped titania oxide might be more effective than an impeller 406 coated with pure titania oxide coating. Accordingly, the illuminators 408 may also be tuned, spectral shifted, or otherwise optimized to enhance the PCO activity specific to the coating of the impeller 406. In some cases, the impeller 406 may be a cross-flow fan, backward centrifugal fan, axial fan, or other type of fan.

In the current example, the air may be input via an in-take manifold 412 on the bottom of surface of the system 402 and output via one or more exhaust manifolds 414 (or air flow diverter) on top of the system 402 as shown. The system 402 may also include ventilation fins 422 along a main body 418 that may include a reflective film along the top surface. The system 402 may also include a ventilated compartment 420 for housing various environmental sensors, as discussed herein, usable to determine the dosage protocol or levels associated with the illuminators 408 and/or 416 as well as, in some cases, the controller.

FIGS. 8-11 illustrates example **800*f*-1100 of a second environmental quality system 802 according to some implementations. In the current example, the system 802 may include an air quality components integrated into a ceiling or industrial style fan. In this example, the blades 804 of the fan may be equipped with the air quality components, as discussed below. For instance, the blades 804 may be modified with respect to conventional fan blades in order to accommodate for upper air disinfection via specialized illuminators or light sources 806 (e.g., LEDs or the like) positioned directly on the blades 804 and oriented upwards. In some cases, additional illuminators 810 may be accommodated or located within a transverse slot 808 that may be machined into the blades defining a cavity that allows the illuminators 810 to irradiate directly on a treated surface 812 (e.g., coated with a PCO layer) of the system 802 in closed proximity to the illuminators 810**.

During nominal operation, the upper air germicidal illuminators 806 disinfect the air mass engulfing the blades 804 with a dosage defined by the intensity of the illuminators 806 and the rotational speed of the blades 804 (which define the dwell time in which air mass flow interacts with the electromagnetic source of irradiance). Similarly, the transverse slot 808 machined into the blades 804 diverts a portion of the air interacting with the blade 804—turbulent mixing at the point of entry and exit of this chamber, generally indicated by arrows 814, which is treated via the PCO engine defined by the illuminators 810 and treated surface 812 integrated into this cavity defined by the slot 808.

In the current example, the system 802 may also include a wing 816 placed on the top surface of the blade 804. Alternatively, the wing 816 may be positioned below the bottom surface of the blade 804. The wing 816 defines a cavity 818 that accommodates additional illuminators 820 positioned to irradiate a bottom surface 822 of the wing 816. The bottom surface 822 may also be treated (e.g., coated with a PCO layer) to establish a PCO engine (in which the air flow through this chamber is defined by the rotational speed of the fan).

As discussed herein, the controller (not shown) may tune the irradiance spectrum of the illuminators 818 and/or 810 together with the rotational speed of the blades 804 in order to increase the efficacy of the PCO engines. It should be understood, that in the current example both a transverse slot 808 system and a wing 816 system are integrated into the blades 804 of the system 802. However, it should be understood that in some implementations, the blades 804 may include either the transverse slot 808 system or a wing 816 system. In some cases, different blades 804 of the system 802 may incorporate different systems (e.g., some blades 804 include the transverse slot 808 system and other blades 804 include the wing 816 system).

FIGS. 12-15 illustrates examples 1200-1500 of a third environmental quality system according to some implementations. In these examples, a portable environmental quality system 1202 is shown. The current example system 1202 may be similar to other implementations discussed herein while having a reduced size, dimensions, or footprint to allow for increased portability. Accordingly, the system 1202 is a compact and lower power unit (such as operating with direct current power) and suitable for portable and automotive applications (such as public transportation systems).

The system 1202 may include POC illuminators 1204 configured within a chamber 1206 housing an impeller 1208 to irradiate directly on a treated surface (e.g., coated with a PCO layer) of the impeller 1208 or other surface of the chamber 1206 in closed proximity to the illuminators 1206. The system 1202 may also include germicidal illuminators 1210 to irradiate the air, indicated by arrows 1212, being output by the exhaust manifold 1214. In some cases, the germicidal illuminators 1210 disinfect the air mass 1212 exhausted by the system 1202 with a dosage defined by the intensity of the illuminators 1212 and the speed of the airflow. Similarly, POC illuminators 1204 treat the airflow within the chamber 1206 with a dosage defined by the intensity of the illuminators 1204 and a speed of a perpendicular inward airflow, generally indicated by arrows 1216, within the chamber 1206.

A controller may control characteristics of the illuminators 1204 and 1210 as well as a speed of a mechanical drive unit 1218 coupled to the impeller 1208. In this manner, the controller may determine a dosage protocol from sensor data generated by sensors, generally indicated by 1220. The controller may then determine based on the dosage protocol control signals for the illuminators 1204 and 1210 and the mechanical drive unit 1218. In this example, the mechanical drive unit 1218 may be powered by a power source 1222.

In the current example, the system 1202 includes a base 1230 and a cover 1224. The cover may include a main intake grid 1226 for allowing air from the environment to enter the chamber 1206 and a sensor intake grid 1228 to allow the sensor 1220 to sample the air from the environment.

FIGS. 16-19 illustrates examples 1600-1900 of a fourth environmental quality system according to some implementations. In the current example, an environmental quality system 1602 may include an upper air germicidal illuminator with integrated PCO treatment unit and may operator similarly to the environmental quality system 402 discussed above. For example, the system 1602 may operate with one or more cross-flow impellers 1604 and the system 1602 is designed as an upper air unit per ASHRAE definitions, in which germicidal illuminators are installed at a designated height (such that individuals within an environment are not direct exposure to the germicidal wavelength irradiation).

In the current example, germicidal illuminators 1606 are oriented upwards projecting the irradiation towards the ceiling and upper portion of an environment. In some cases, the germicidal illuminators 1606 may irradiate air as the air is exhausted from the impeller chamber via an exhaust manifold 1608. The system 1602 also incorporates a PCO engine intended to serve as source for the mineralization of total volatile organic matter and odors and the like (e.g., by way of mineralization via the photocatalytic oxidation activity of a ceramic coating applied onto the fan's impeller, as discussed herein). In this particular example, the impeller 1604 has a form of a cross-flow fan and may be coated with a with a photocatalytic oxidizing layer that may mineralize the VOC and odors within the air when irradiated by the POC illuminators 1610.

As discussed above, a controller together with one or more machine learned models or networks may determine a dosage protocol based at least in part on sensor data representing a current state of the environment. The controller may then apply the dosage protocol based at least in part by adjusting characteristics of the illuminators 1606 and/or 1610 as well as a rational speed of the impeller 1604. As one illustrative example, in the event that the environment is unoccupied as determined by the sensor data, the system 1602 may operate as air purification unit, thereby running the PCO illuminators 1610 and the impeller 1604 (e.g., the PCO engine) while disabling the germicidal illuminators 1606. In the event that anthropogenic activity is detected, the germicidal portion of the embodiment is activated.

In the current example, a housing 1612 of the system 1602 may have an airfoil shaping envelop structure 1618. The housing 1612 may include an intake area 1614 and two exhaust manifolds 1608 and 1616 on either side of the airfoil shaping envelop structure 1618.

In the above examples and implementations of FIGS. 2-20 the environmental quality systems are discussed with respect to treating air. However, it should be understood by one skilled in the art that the systems, methods, and processes may be applied to treating fluids (such as water) in a similar manner. Accordingly, the systems of FIGS. 1-20 may be applied to treat or process air, gases, fluids, water, and the like as discussed herein. For example, the systems may include an intake area for receiving the fluids or gases and exhaust manifold for outputting the fluids or gases. The system may also include by a PCO engine and/or germicidal engine including illuminators and/or an impeller and/or chamber treated with a photocatalytic oxidation layer.

As one illustrative example, a water based environmental quality system may be tuned based on environmental sensing (e.g., one or more water quality sensors, such as temperature sensors, color sensors, particle sensors, pH sensors, conductivity sensors, and the like) as well as know variables, such as pH level, electrical conductivity in water, total dissolved solids level, turbidity, dissolved gases, color sensing, and the like. The water based system may include distinctive UV illuminators or light sources, a volume defined by a chamber geometry, in which maximum irradiance levels are attained, and, in some instances, secondary illuminators or light sources and one or more mechanical actuator in the form of propellers, submersed pumps, external pumps, or the like.

The water based system may also operate in modes as previously described above (e.g., as a germicidal disinfection devices and as a purifier via the reaction of the UV irradiance in different bands interacting with photocatalytic oxidizing coatings applied to the inner walls of the chamber, rotating or moving parts of the mechanical actuator such as impellers or propellers, and similar components). In one implementation, the water based system is fully submersible with the illuminators or light sources such as LEDs housed within watertight compartment with one or more transparent windows or panels. The windows may have above a threshold level of UV transmittance (such as high purity fused quartz glass components). Moreover, the compartment may be configured in the form of a subcomponent of the treatment chamber, such that medium treated (water or any other liquid or gas) may be exposed to maximum irradiance levels while reducing the energy input to the system.

Due to low energy consumption, this system is ideal for battery operations and photovoltaic or other renewable energy sources applications in which there limited or absence of "mains or shore" power sources as rural or remote locations, swimming pools, fish tanks, or even applications such as the water treatment in airplanes or ships.

In another embodiment, the water based system may be adapted to water filtration systems, as pre-filtering or post-filtering stage such as the ones used in commercial and residential applications and typically installed at the service entrance of the facility. An example of such implementation consists of a well pump and storage system, which makes use of a filtering stage to reduce suspended sediments that, if nor removed, will absorbed a high amount the UV irradiance. The water based system, in some cases, may be inserted into the same vessel or tank defining the filtering stage or adapted as a self-contained assembly in the form of a secondary or post-filtering stage.

The water based system may also be constructed in the form of individual and fully contained standalone assemblies (herein "UV treatment cells") that may be interconnected in tandem configurations or parallel configurations such that a targeted UV dosage is attained as function of a certain flow requirement. If more than one mechanical actuator is used in the system or assembly to control the flow rate, these mechanical actuators may be synchronized via a user control unit, such as described above with respect to FIGS. 1-20. In this example, the control unit may sense the water parameters and if determined that an above average (elevated) dosage is required due the detection of specific (e.g., more UV resilient) microorganisms or certain chemical compounds, additional UV treatment cells are activated.

The use of the UV treatment cells allows for automating the control of the dosage imparted to the medium being treated and for the implementation of very effective energy conservation schemes or operating modes. It follows that a tandem or series results into the most simplistic configuration in which one or more UV treatment cells are used, as the follow is maintained constant through the cell array, the UV illuminators or light sources are simply modulated in output or simply, turned ON or OFF as needed. But, when multiple UV treatment cells are connected in parallel, the use of control valves associated to individual or cluster of cells might be required in order to maintain and control the required flow rates.

Although the subject matter has been described in language specific to structural features, it is to be understood that the subject matter defined in the appended claims is not necessarily limited to the specific features described. Rather, the specific features are disclosed as illustrative forms of implementing the claims.

EXAMPLE CLAUSES

A. An adaptive autonomous lighting luminaire or system that operates within the full UV spectrum by independently exerting control of groups of light sources with distinctive irradiation and spectral responses.

B. An adaptive autonomous lighting luminaire or system that operates within the full UV spectrum by independently exerting control of groups of light sources to generate polychromatic irradiance output.

C. A lighting luminaire or system operating within the full UV spectrum relying on the use of different sensors associated to a controller; the controller configured to adjust the irradiance levels within the different UV bands being implemented in a decoupled and independent way.

D. The lighting luminaire of claim C, wherein: the controller implements the UV bands as at least one of the following: only UVA, only UVC, UVC+222 nm, or UVA+UVC.

E. A lighting luminaire or system exerting independent and decoupled control over distinctive groups of UV light sources with unique reliability performance level and distinctive lifespan to provide ad-hoc control of each group of distinctive UV light sources such that the overall reliability performance and life-span of the assembly is increased.

F. A lighting luminaire or system that operates within the full UV spectrum and exerts control over different groups of specialized UV lighting sources with the purpose of optimizing the energy consumption of the lighting luminaire or system by delivering dosage specific to each UV band of interest on an "as needed" basis.

G. A photocatalytic oxidation reactor engine comprising a photocatalytic oxidation reactor irradiated with UVA LEDs or a combination of UVA+UVC light at irradiance levels determined by the output signal/data provided by indoor air quality or environmental sensors, while concurrently controlling the irradiance levels of decoupled germicidal light sources built into the luminaire or lighting system; the control of the light sources is also governed by the response of one or more sensors that assess the levels of nearby anthropogenic activity.

H. A system for use in horticultural applications in which groups of light sources within specific UV bands irradiate the crops and associated surfaces to control the growth rate of the crops by impacting the crops photo morphism cycles and by delivering the proper UVC dosage as part of a germicidal surface disinfection strategy.

I. The system of H, fitted with secondary UVC light sources that are activated once airborne spores and other pathogens are detected using particulate matter sensors type PM 1.0/2.5/10.0 micrometer particle counters. These secondary light sources are either associated with an air disinfection chamber or are operated as direct radiators projecting light upwards into the surroundings of the luminaire of lighting system.

J. An air disinfection system or germicidal UVC system in which the irradiance output levels are adjusted to match optimum operating conditions based on environmental data provided by temperature and humidity sensors associated to the luminaire of lighting system.

K. A system utilizing specialized sensors associated to a luminaire or lighting system grouped mainly into sensors that directly correlate to indoor air quality levels and sensors that correlate to anthropogenic activity, allowing to control a PCO reactor and germicidal UV light sources in a decoupled and independent way, based on the output of these groups of sensors.

L. The system of K, further comprising an occupancy sensors to control optional visible light spectrum sources.

M. The system of K, further comprising, a smart controller based on a microprocessor or microcontroller-based architecture that, in combination with the output produce by the occupancy sensors, allows for the use of machining learning models and/or networks that allow for the selection of the irradiance levels and dosage applied within the different UV bands.

N. An adaptive autonomous lighting luminaire or system of A, B, C, or D, fitted with a communication board that provides connectivity to the luminaire of lighting system in the form of wired and wireless interface and allows for the embodiment to be controlled via downloadable applications, building management systems, SCADA consoles and/or cloud-based services.

O. An adaptive autonomous lighting luminaire or system of A, B, C, or D, further comprising an adaptation module or sub-system that is coupled to standard lighting form factors including at least one of a high-bay fixture, a low-bay fixture, a troffer, or an acorn bulb-like fixture.

P. A environmental quality system comprising a controller configured to control the dosage applied to an air mass flowing through or near the system, by controlling the rotational speed of the fan used as source of forced ventilation and the output intensity of the light sources under consideration.

Q. The environmental quality system of P, wherein the controller is configured for self-adjusting and/or self-regulating based on data received from sensors and a logic controller associated with a physical environment surrounding the environmental quality system.

R. A fan impeller coated with a photocatalytic oxidizing (PCO) ceramic layer that can be replaced in-situ, such that an impeller optimized coating can be used instead, based on the measured air quality characteristics. This allowing for these novel devices to be upgraded after installed in the fields.

S. An adaptive autonomous lighting luminaire or system that operates within the full UV spectrum by independently exerting control of groups of light sources with distinctive irradiation and spectral responses including a PCO engine associated with a fluid tank exposed to direct sunlight, allowing for the use of photovoltaic or similar renewable energy sources.

T. The adaptive autonomous lighting luminaire or system of S that operates via renewable energy sources include at least one of photovoltaic or hydroelectric.

U. The adaptive autonomous lighting luminaire or system of T wherein the system is installed within the fluids of the tank and operates at reduced energy consumption when submerged.

V. The adaptive autonomous lighting luminaire or system of T wherein the system is installed in a drain or supply valve associated with the tank. W. The adaptive autonomous lighting luminaire or system of S that operates via battery packs or power storage device for portable applications and energy constrained application such as commercial aviation and similar implementations.

While the example clauses described above are described with respect to one particular implementation, it should be understood that, in the context of this document, the content of the example clauses can also be implemented via a method, device, system, a computer-readable medium, and/or another implementation. Additionally, any of examples A-W may be implemented alone or in combination with any other one or more of the examples A-W.

What is claimed is:

1. A system for improving a quality of an air mass proximate to the system comprising:

a first group of illuminators outputting irradiation within a first portion of an ultraviolet (UV) spectrum;

a second group of illuminators outputting irradiation within a second portion of the UV spectrum;

one or more environmental sensors configured to generate data associated with the air mass proximate to the system; and a controller to independently control characteristics of the first group of illuminators and the second group of illuminators based at least in part on the data; and wherein the system is incorporated into a blade of a fan and the controller determines the characteristics based at least in part on a rotational speed of the fan.

2. The system for improving the quality of the air mass of claim 1, wherein the first portion of the UV spectrum overlaps with the second portion of the UV spectrum.

3. The system for improving the quality of the air mass of claim 1, wherein the first portion of the UV spectrum and the second portion of the UV spectrum output irradiation covering a full UV spectrum.

4. The system for improving the quality of the air mass of claim 1, wherein the first portion of the UV spectrum differs from the second portion of the UV spectrum.

5. The system for improving the quality of the air mass of claim 1, wherein the one or more environmental sensors comprises at least one of:

a temperature sensor, a humidity sensor, a volatile organic compound (VOC) sensors=, a carbon dioxide (CO2) sensor, an occupancy sensor;

a motion sensor; or a particulate matter sensor.

6. The system for improving the quality of the air mass of claim 1, wherein the controller is configured to input the data into one or more machine learning models or networks and the controller receives the characteristics as an output of the one or more machine learning models or networks.

7. The system for improving the quality of the air mass of claim 1, wherein the controller is configured to determine a dosage protocol associated with the air mass based at least in part on the data and the characteristics of the first group of illuminators and the second group of illuminators are selected to apply the dosage protocol to the air mass.

8. The system for improving the quality of the air mass of claim 1, wherein:

the blade includes a wing positioned along a top surface of the blade, a bottom surface of the wing coated with a photocatalytic oxidizing (PCO) layer;

the first group of illuminators are positioned along a top surface of the blade beneath the wing to irradiate the bottom surface of the wing; and the second group of illuminators are positioned along a top surface of the blade unobstructed by the wing to irradiate in a substantially upward direction.

9. The system for improving the quality of the air mass of claim 1, wherein:

the blade includes a transverse slot, the transverse slot having at least one surface coated with a photocatalytic oxidizing (PCO) layer;

the first group of illuminators are positioned within the transverse slot to irradiate the at least one surface; and the second group of illuminators are positioned along a top surface of the blade to irradiate in a substantially upward direction.

10. The system for improving the quality of the air mass of claim 1, wherein:

the system is incorporated into a housing for a conventional light, the housing having an intake manifold, a chamber, an impeller within the chamber, and a bifurcated exhaust manifold;

the impeller or an interior surface of the chamber is coated with a photocatalytic oxidizing (PCO) layer;

the first group of illuminators are positioned within the chamber to irradiate the impeller or interior surface; and the second group of illuminators are positioned within the exhaust manifold to irradiate in a substantially upward direction.

11. The system for improving the quality of the air mass of claim 10, wherein the conventional light is at least one of a high-bay fixture, a low-bay fixture, a troffer, or an acorn blub-like fixture.

12. The system for improving the quality of the air mass of claim 10, wherein the impeller is releasably coupled to the system.

13. The system for improving the quality of the air mass of claim 1, further comprising a communication interface to allow the controller to communicatively couple to a downloadable application operation on a host user device or a cloud-based service.

14. The system for improving the quality of the air mass of claim 1, wherein the first group of illuminators are associated with a germicidal engine and the second group of illuminators are associated with a photocatalytic oxidizing (PCO) engine.

15. The system for improving the quality of the air mass of claim 1, wherein either the first group of illuminators outputting irradiation or the second group of illuminators are positioned with respect to one or more horticultural units to irradiate foliage associated with the horticultural units.

16. A method for improving a quality of an air mass comprising:

receiving first sensor data from a first sensor within a physical environment;

receiving second sensor data from a second sensor within the physical environment, the second sensor of a different type than the first sensor;

determining, based at least in part on the first sensor data, a first characteristic of an output of a first group of illuminators; and determining, based at least in part on the second sensor data, a second characteristic of an output of a first group of illuminators; and wherein the first group of illuminators are associated with a germicidal engine and the second group of illuminators are associated with a photocatalytic oxidizing (PCO) engine.

17. The method for improving the quality of the air mass of claim 16, wherein:

determining the first characteristic of the output of the first group of illuminators further comprises inputting the first sensor data into a first machine learned model or network and receiving the first characteristic as an output of the first machine learned model or network; and determining the second characteristic of the output of the second group of illuminators further comprises inputting the second sensor data into a second machine learned model or network and receiving the second characteristic as an output of the second machine learned model or network.

18. The method for improving the quality of the air mass of claim 16, wherein determining the second characteristic of the output of the second group of illuminators is based at least in part on a dwell time associated with the air mass within a chamber of an environmental quality system, the chamber housing an impeller and the second group of illuminators.

19. The method for improving the quality of the air mass of claim 16, wherein the first sensor data is associated with an air quality level of an air mass of the physical environment and the second sensor data is associated with anthropogenic activity within the air mass of the physical environment.

20. The method for improving the quality of the air mass of claim 16, further comprising:

receiving a rotational speed of a fan; and wherein at least one of determining the first characteristic or determining the second characteristic is based at least in part on the rotational speed of the fan.

* * * * *